US011600089B2

(12) United States Patent
Abraham et al.

(10) Patent No.: US 11,600,089 B2
(45) Date of Patent: Mar. 7, 2023

(54) SYSTEMS AND METHODS FOR PROCEDURE OPTIMIZATION

(71) Applicant: Microsoft Technology Licensing, LLC, Redmond, WA (US)

(72) Inventors: Robin Abraham, Redmond, WA (US); Liang Du, Redmond, WA (US); Zeeshan Ahmed, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 227 days.

(21) Appl. No.: 17/160,188

(22) Filed: Jan. 27, 2021

(65) Prior Publication Data
US 2022/0237422 A1    Jul. 28, 2022

(51) Int. Cl.
| G06F 40/30 | (2020.01) |
| G06F 40/35 | (2020.01) |
| G16H 10/20 | (2018.01) |
| G16H 50/70 | (2018.01) |
| G06V 30/262 | (2022.01) |
| G06F 40/279 | (2020.01) |

(52) U.S. Cl.
CPC .......... *G06V 30/274* (2022.01); *G06F 40/279* (2020.01); *G06F 40/30* (2020.01); *G16H 10/20* (2018.01)

(58) Field of Classification Search
CPC ........ G06F 30/279; G06F 40/30; G06F 40/35; G16H 10/20; G16H 50/70; G16H 70/20

USPC .................................... 704/1, 9; 705/2, 7.37
See application file for complete search history.

(56) References Cited

U.S. PATENT DOCUMENTS

| 11,074,918 B2 * | 7/2021 | Herbach .................. G06F 40/30 |
| 11,176,326 B2 * | 11/2021 | Stevens .................... G06F 40/30 |
| 2020/0194131 A1 * | 6/2020 | Stevens ................... G16H 70/20 |
| 2020/0273547 A1 * | 8/2020 | Will ........................ G06F 40/30 |
| 2021/0174027 A1 * | 6/2021 | Ambati .................... G06F 40/30 |
| 2022/0171935 A1 * | 6/2022 | Goyal ...................... G06F 40/35 |
| 2022/0237382 A1 * | 7/2022 | Abraham ................ G06F 40/30 |

\* cited by examiner

*Primary Examiner* — Martin Lerner
(74) *Attorney, Agent, or Firm* — Workman Nydegger

(57) ABSTRACT

Procedural optimization is facilitated by receiving user input for creating or modifying a body of text comprising a procedure, detecting one or more procedural steps associated with the procedure using a procedural step detection module, automatically searching within a corpus of references for one or more related procedural steps using a related procedural step extraction module, automatically identifying one or more outcomes within the corpus of references associated with the one or more related procedural steps using an outcome extraction module, automatically determining whether the one or more outcomes comprise detrimental results using an outcome analysis module, and, in response to determining a set of detrimental outcomes from the one or more outcomes that comprise detrimental results, presenting a detriment indicator within the user interface in association with the one or more procedural steps.

20 Claims, 18 Drawing Sheets

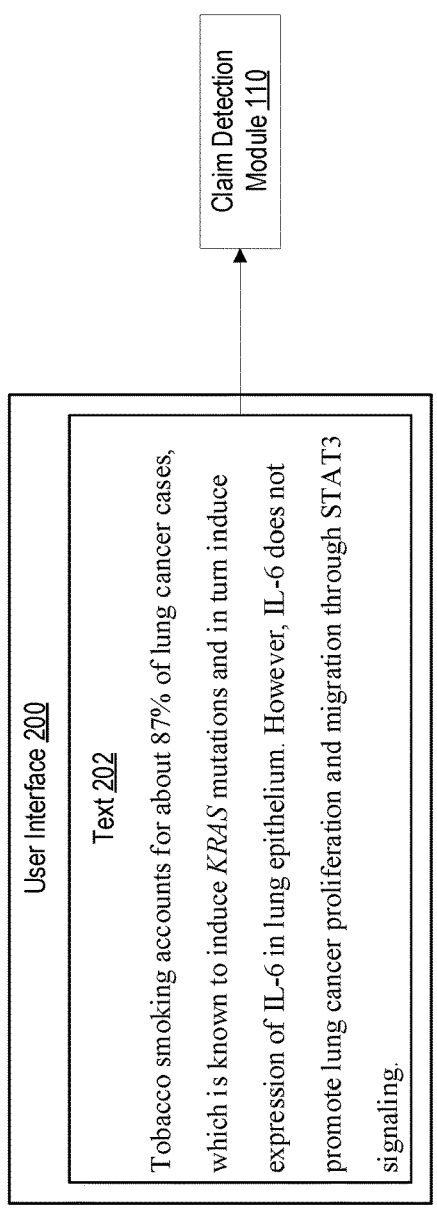
FIG. 2A
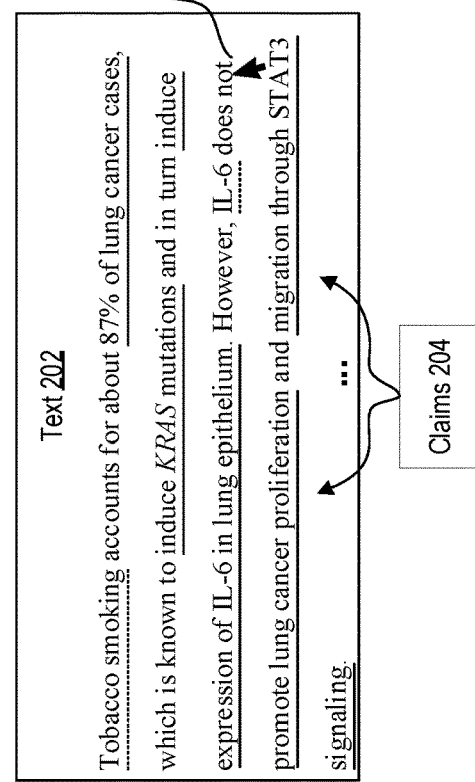
FIG. 2B
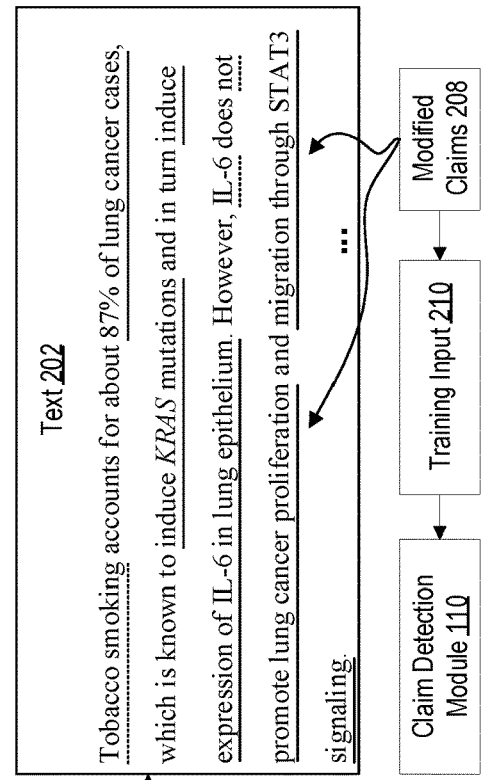

SYSTEMS AND METHODS FOR PROCEDURE OPTIMIZATION

BACKGROUND

In many content production industries, claims or assertions made by authors or content creators are expected to be supported by known facts and/or available evidence. By way of example, it is typical for research proposals, research papers, advertising materials, news, and other publications to make claims or assertions that are supported by facts and/or evidence.

When preparing the content to be published, content creators often need to familiarize themselves with existing works, evidence, and/or facts. In some instances, when making a claim or assertion in an original work, content creators often need to be able to make citations to particular references or particular statements, data, assertions, and/or claims made in already existing works.

However, content creators are often limited in the claims or assertions that they can make by the existing facts or evidence of which the content creators have personal knowledge. For example, an individual writing a formal research paper may be limited to making assertions that draw from content that the individual has already read, tagged, and/or archived for use while writing the formal research paper. Individuals and entities are limited in the amount of content that they can perceive and retain for future use while creating original content. Thus, the foregoing limitations present a problem in content creation.

Furthermore, many content creators create content that is associated with procedures or decision-making, such as standard operating procedures (SOPS), clinical trial protocols, and others. It can be advantageous for such content creators to be familiar with outcomes associated with past procedures or protocols so as to discern which procedural steps resulted in advantageous or desired outcomes and which procedural steps resulted in detrimental or undesired outcomes. In this way, a content creator creating a novel procedure may include procedural steps that are associated with advantageous outcomes and may refrain from including procedural steps that are associated with detrimental outcomes.

However, content creators of content associated with procedures or decision-making are similarly limited in the number of prior procedures and associated outcomes they can familiarize themselves with in preparation for generating new procedures. Such limitations present a problem in procedure creation and may allow undesirable procedures to be carried through into future procedures.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments are directed at least to systems and methods that facilitate procedure optimization for procedures present in bodies of text.

Some embodiments include a system for facilitating optimization of procedures. The system includes one or more processors and one or more hardware storage devices storing instructions that are executable by the one or more processors to configure the system to perform various acts.

In some instances, the system is configured to receive, within a user interface, user input for creating or modifying a body of text comprising a procedure. The system is also configured, in some instances, to detect one or more procedural steps associated with the procedure using a procedural step detection module having been trained to detect procedural steps within bodies of text. The system is further configured, in some instances, to automatically search within a corpus of references for one or more related procedural steps using a related procedural step extraction module having been trained to identify related procedural steps based on content of detected procedural steps. The one or more related procedural steps are determined by the related procedural step extraction module to be relevant to the one or more procedural steps.

The system is also configured, in some instances, in response to identifying the one or more related procedural steps, to automatically identify one or more outcomes within the corpus of references associated with the one or more related procedural steps using an outcome extraction module having been trained to identify outcomes that are associated with identified procedural steps.

Furthermore, in some instances, the system is configured to automatically determine whether the one or more outcomes comprise detrimental results using an outcome analysis module having been trained to identify whether results associated with identified outcomes are detrimental.

In some instances, the system is configured to, in response to determining a set of detrimental outcomes associated with detrimental results, present a detriment indicator within the user interface in association with the one or more procedural steps. The detriment indicator indicates that the one or more procedural steps are associated with detrimental results.

In some instances, the system is configured to receive a document comprising a body of text, and to detect one or more procedural steps associated with a procedure in the text, as well as to automatically search within a corpus of references for one or more related procedural steps using a related procedural step extraction module having been trained to identify related procedural steps based on content of detected procedural steps. The one or more related procedural steps are determined by the related procedural step extraction module to be relevant to the one or more procedural steps.

In some instances, the system is configured, in response to identifying the one or more related procedural steps, to automatically identify one or more outcomes within the corpus of references associated with the one or more related procedural steps using an outcome extraction module having been trained to identify outcomes that are associated with identified procedural steps.

In some instances, the system is configured to automatically determine whether the one or more outcomes comprise detrimental results using an outcome analysis module having been trained to identify one or more results associated with identified outcomes and determine whether the one or more results are detrimental. Furthermore, in some instances, the system is configured, in response to determining a set of detrimental outcomes from the one or more outcomes that comprise detrimental results, to generate a modified document that includes a detriment indicator in association with the one or more procedural steps. The detriment indicator indicates that the one or more procedural steps are associated with detrimental outcomes.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIGS. 2A and 2B illustrate an example of detecting claims within a body of text using a claim detection module;

DETAILED DESCRIPTION

Figure 1:
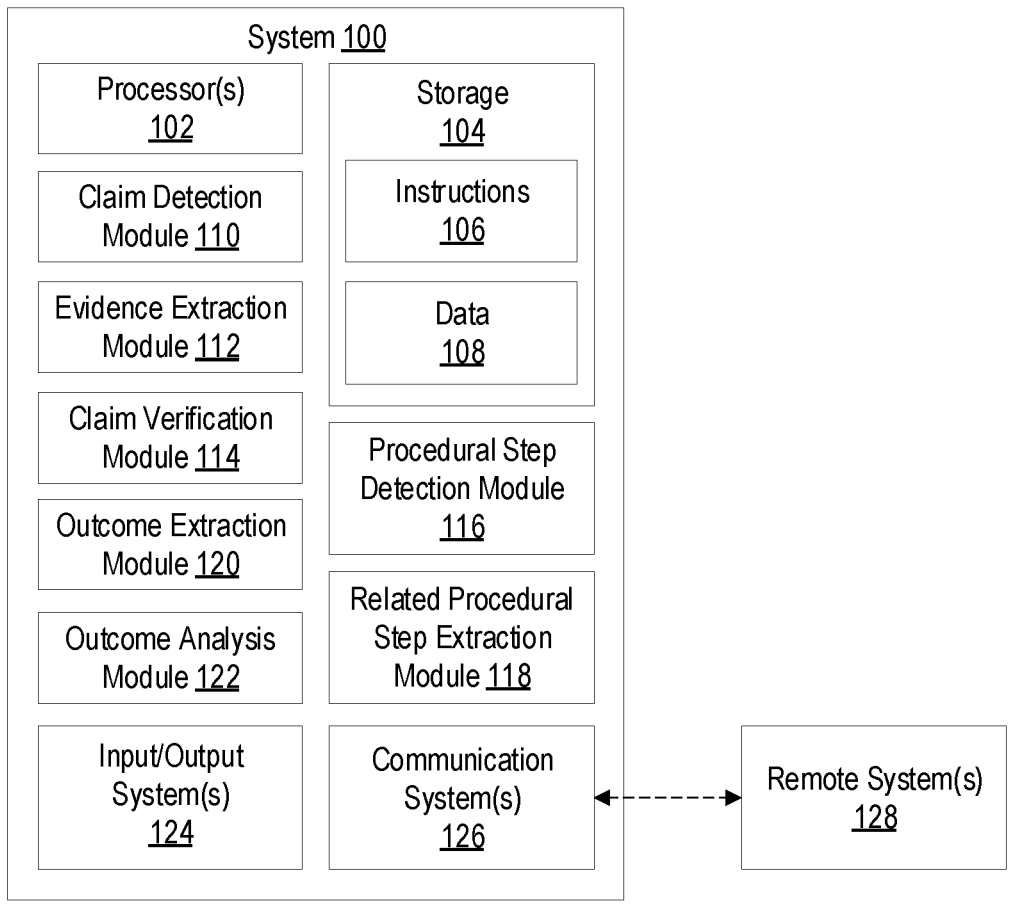
FIG. 1 illustrates example components of an example system that may include or be used to implement one or more disclosed embodiments.

Disclosed embodiments are generally directed at least to systems and methods for facilitating procedure optimization.

Examples of Technical Benefits, Improvements, and Practical Applications

Those skilled in the art will recognize, in view of the present disclosure, that at least some of the disclosed embodiments may be implemented to provide improved systems and methods for verifying claims and/or optimizing procedures present in textual content. The following section outlines some example improvements and/or practical applications provided by the disclosed embodiments. It will be appreciated, however, that the following are examples only and that the embodiments described herein are in no way limited to the example improvements discussed herein.

Implementations of the present disclosure may allow content creators create content in a manner that circumvents the limitations of the content creator's personal knowledge. For example, implementations of the present disclosure may allow users to draw from a corpus of references or knowledge repositories when creating or viewing textual content, regardless of whether the user is personally familiar with the references represented in the corpus of references. Furthermore, at least some implementations of the present disclosure link claims or procedures detected in a body of text to relevant content from the corpus of references and selectively display the relevant content in association with the linked claims, allowing users to refer to and/or increase familiarity with relevant content from the corpus of references.

In view of the foregoing, users may, in some instances, remain privy to advancements made in various fields of study and/or disciplines. For example, in a document authoring context, a user may author an assertion based on their current understanding of the state of the art in a particular field of study. However, unbeknownst to the user, an advancement may have occurred in the particular field of study refuting the assertion authored by the user. At least some implementations of the present disclosure are configured to or configurable to automatically detect that the assertion is refuted by the latest evidence and inform the user of such a detection, thereby allowing the user to bring their assertion into conformity with the latest evidence.

Thus, implementations of the present disclosure may help authors to avoid the embarrassment and/or liability that may arise from publishing unsupported claims and can serve to improve the accuracy of created content. Implementations of the present disclosure may also help entities avoid resource waste that can result from the presentation of unsubstantiated claims. For example, in the context of drug advertising, individuals who initially draft advertisements for novel drugs often have marketing training but are not experts in the medical field or the legal field. Accordingly, such individuals are often unfamiliar with the types of claims that can be made about a novel drug that are adequately supported by available evidence (e.g., based on drug testing) and that are permitted by applicable law. Although advertisements initially drafted by such individuals may eventually be reviewed by reviewers that are experts in determining whether an advertisement is permissible in view of available evidence and applicable law, significant amounts of resources are wasted in moving an unsubstantiated or unsupported advertisement through an advertisement generation pipeline to be reviewed by an expert reviewer, only to be rejected by the expert reviewer. To avoid such waste, implementations of the present disclosure can bring the relevant knowledge for determining whether an advertisement is permissible to the individual who initially drafts the advertisement. Accordingly, implementations of the present disclosure may allow the individual initially drafting the advertisement to make front end corrections to the advertisement based on available evidence and/or applicable law, thereby saving resources that would otherwise become wasted in moving a faulty advertisement through an advertisement generation pipeline for final review.

As another example, in a document authoring context, a user may author a particular procedural step based on their current understanding of the state of the art in a particular field of study. However, unbeknownst to the user, an advancement may have occurred in the particular field of study indicating that the particular procedural step authored by the user is associated with detrimental results. At least some implementations of the present disclosure are configured to or configurable to automatically detect that the particular procedural step is associated with detrimental results and inform the user of such a detection, thereby allowing the user to bring their procedural step into conformity with the latest evidence.

In view of the foregoing, users may, in some instances, create procedures that are not associated with detrimental results in view of available evidence, even where the user is not personally aware of all available evidence. For instance, in a clinical trial protocol context, users often generate a novel clinical trial protocol by modifying an existing clinical trial protocol. Implementations of the present disclosure may allow users to be made aware when treatment steps of an existing clinical trial protocol have been determined by advancing research to be associated with detrimental patient outcomes. Users may thus advantageously omit such treatment steps from novel clinical trial protocols.

Having just described some of the various high-level features and benefits of the disclosed embodiments, attention will now be directed to FIGS. 1 through 18. These Figures illustrate various conceptual representations, architectures, methods, and supporting illustrations related to the disclosed embodiments. Also, with regard to referenced systems that are "configurable to" perform certain functionality, it will be appreciated that such references should also be interpreted to cover corresponding systems that are completely configured to perform the referenced functionality, as well as systems that actively perform the referenced functionality.

Example Systems

Attention is now directed to FIG. 1, which illustrates an example system 100 that may include or be used to implement one or more disclosed embodiments. In some instances, the system 100 is implemented as one or more general-purpose or special purpose computing systems, which may take on a variety of forms.

FIG. 1 illustrates various example components of the system 100. For example, FIG. 1 illustrates an implementation in which the system includes processor(s) 102, storage 104, input/output system(s) 124 (I/O system(s) 124), and communication system(s) 126. FIG. 1 also illustrates that a system may include or be used to implement various modules, including one or more of a claim detection module 110, an evidence extraction module 112, a claim verification module 114, a procedural step detection module 116, a related procedural step extraction module, an outcome extraction module 120, and an outcome analysis module. Although FIG. 1 illustrates a system 100 as including particular components, one will appreciate, in view of the present disclosure, that a system 100 may comprise any number of additional or alternative components.

As used herein, the terms "executable module," "executable component," "component," "module," or "engine" can refer to any combination of hardware components or software objects, routines, or methods that may configure a computer system 100 to carry out certain acts. For instance, the different components, modules, engines, devices, and/or services described herein may be implemented utilizing one or more objects or processors that execute on computer system 100 (e.g., as separate threads). While FIG. 1 depicts several independent modules 110, 112 114, 116, 118, 120, and 122 one will understand the characterization of a module is at least somewhat arbitrary. In at least one implementation, the various modules 110, 112 114, 116, 118, 120, and 122 of FIG. 1 may be combined, divided, or excluded in configurations other than that which is shown. For example, any of the functions described herein with reference to any particular module 110, 112 114, 116, 118, 120, and 122 may be performed utilizing any number and/or combination of processing units, software objects, modules, instructions, computing centers (e.g., computing centers that are remote to computing system 100), etcetera. As used herein, the individual modules 110, 112 114, 116, 118, 120, and 122 are provided for the sake of clarity and explanation and are not intended to be limiting.

The processor(s) 102 may comprise one or more sets of electronic circuitry that include any number of logic units, registers, and/or control units to facilitate the execution of computer-readable instructions (e.g., instructions that form a computer program). Such computer-readable instructions may be stored within storage 104. The storage 104 may comprise physical system memory (e.g., one or more hardware storage devices) and may be volatile, non-volatile, or some combination thereof. Furthermore, storage 104 may comprise local storage, remote storage (e.g., accessible via communication system(s) 126 or otherwise), or some combination thereof. Additional details related to processors (e.g., processor(s) 102) and computer storage media (e.g., storage 104) will be provided hereinafter.

In some implementations, the processor(s) 102 and/or modules 110, 112 114, 116, 118, 120, and 122 described herein may comprise or be configurable to execute any combination of software and/or hardware components that are operable to facilitate processing using machine learning models or other artificial intelligence-based structures/architectures that are integrated into and/or that comprise the referenced modules.

By way of example, processor(s) 102 and/or modules 110, 112 114, 116, 118, 120, and 122 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 and/or modules 110, 112 114, 116, 118, 120, and 122 may be configured to execute instructions 106 stored within storage 104 to perform certain actions associated with claim verification and/or procedure optimization. For instance, such actions may be associated with detecting claims present within text (e.g., via processor(s) 102 and/or claim detection module 110), extracting evidence related to a detected claim from a repository of references (e.g., via processor(s) 102 and/or evidence extraction module 112), verifying detected claims in view of extracted evidence (e.g., via processor(s) 102 and/or claim verification module 114), detecting procedural steps present within text (e.g., via processor(s) 102 and/or procedural step detection module 116), extracting related procedural steps that are related to a detected procedural step from a repository of references (e.g., via processor(s) 102 and/or related procedural step extraction module 118), extracting outcomes associated a procedural step from a repository of references (e.g., via processor(s) 102 and/or outcome extraction module 120), and/or analyzing outcomes associated with procedural steps (e.g., processor(s) 102 and/or outcome analysis module 122).

In addition, the processor(s) 102 and/or modules 110, 112 114, 116, 118, 120, and 122 may be configured to perform actions associated with training or configuring the modules 110, 112 114, 116, 118, 120, and 122 to perform any functionality described herein. The actions performable by the processor(s) 102 and/or modules 110, 112 114, 116, 118, 120, and 122 may at least partially rely on various types of data 108. For instance, any of the modules 110, 112 114, 116, 118, 120, and 122 described herein may be trained to perform detection, recognition, extraction, verification, and/or analysis tasks on textual content using various types of training data (e.g., domain-specific training data, cross-domain, and/or multi-domain data) and using various types of training techniques (e.g., fully supervised, weakly supervised, and/or unsupervised). For example, one or more modules 110, 112 114, 116, 118, 120, and 122 of the present disclosure may utilize an available language model (e.g., bidirectional encoder representations from transformers (BERT), generative pre-trained transformer 3 (GPT-3) or other versions, Turing, and/or others), and further refinements may be made to the language model via additional training to configure the language model for one or more particular uses. Additional details concerning training and configuring the modules 110, 112 114, 116, 118, 120, and 122 will be provided hereinafter.

In some instances, the actions performable using the processor(s) 102 and/or modules 110, 112 114, 116, 118, 120, and 122 may rely at least in part on communication system(s) 126 for receiving data from remote system(s) 128, which may include, for example, one or more separate systems or computing devices, sensors, and/or others. The communications system(s) 128 may comprise any combination of software or hardware components that are operable to facilitate communication between on-system components/devices and/or with off-system components/devices. For example, the communications system(s) 128 may comprise ports, buses, or other physical connection apparatuses for communicating with other devices/components. Additionally, or alternatively, the communications system(s) 128 may comprise systems/components operable to communicate wirelessly with external systems and/or devices through any suitable communication channel(s), such as, by way of non-limiting example, Bluetooth, ultra-wideband, WLAN, infrared communication, and/or others. For example, implementations of the present disclosure may be practiced using cloud computing.

The remote system(s) 128 store and/or access the referenced corpus of references, documents, text and other documentation/data accessed by the system 100. In some instances, the referenced documents, text, corpus of references and other referenced data is at least partially and/or entirely stored within the system or system storage systems, such as when being implemented within a closed enterprise system and even when implemented in an open and/or distributed system.

As shown, FIG. 1 also illustrates that system 100 may comprise or be in communication with I/O system(s) 124. I/O system(s) 124 may include any type of input or output device such as, by way of non-limiting example, a touch screen, a mouse, a keyboard, a controller, and/or others, without limitation. For example, textual content may be generated in response to user input provided by a keyboard, touch screen, or other I/O system(s) 124, and systems of the present disclosure may detect claims and/or procedural steps present in the textual content.

Example Techniques for Facilitating Claim Verification

Attention is now directed to FIG. 2A, which provides a conceptual representation of detecting claims within a body of text 202 using a claim detection module 110. In particular, FIG. 2A shows a selection of textual content (i.e., text 202) represented within a user interface 200. The user interface 200 may comprise any user interface within which text is perceivable by users, such as a user interface associated with a document authoring or text editing program, a text viewing or navigation program (e.g., an e-book or PDF reader, a web browser), and/or others. The user interface 200 may be viewable by users on a display, a touch screen, and/or other device (e.g., in the form of an I/O system 124). Although the present example focuses, in at least some respects, on text 202 represented within a user interface 200, one will appreciate, in view of the present disclosure, that the techniques described herein may be used to detect claims within textual content regardless of whether the textual content is represented in a user interface. For instance, claims may be detected within a document file received at a server system without displaying any portion of the document file on a user interface.

FIG. 2A shows that the text 202 represented within the user interface 200 includes a particular selection of text that states, "Tobacco smoking accounts for about 87% of lung cancer cases, which is known to induce KRAS mutations and in turn induce expression of IL-6 in lung epithelium. However, IL-6 does not promote lung cancer proliferation and migration through STAT3 signaling." This example selection of text includes various claims or assertions about the relationships between tobacco smoking IL-6 proliferation, and lung cancer. As described herein, systems and methods of the present disclosure are configurable to determine the veracity of claims such as those represented in the text 202 in view of evidence available in a corpus or repository of references. The subject matter and content of the text 202 is provided for the sake of explanation only and is not limiting of the types of textual content on which the techniques of the present disclosure may be utilized.

As indicated above, in some instances, the text 202 is generated by a user within a text authoring context or is navigated to by a user within a text navigation/viewing context. For example, a user navigating a website may come across the text 202 on the website and provide user input selecting the text 202 to verify any claims represented within the text 202. As another example, a user may provide user input generating text including the text 202 and may additionally provide user input selecting the text 202 to verify any claims represented within the text 202. As yet another example, in some instances, rather than providing user input selecting the text 202 for triggering verification of claims therein, claim verification is initiated automatically and/or in real-time as a user authors and/or navigates a body of text.

Regardless of how the text 202 is obtained or identified by a system (e.g., system 100), a system may access a claim detection module 110 to facilitate the automatic identification of claims represented within the body of text. In some implementations, the claim detection module 110 is trained using a set of ground truth data to enable the claim detection module 110 to detect occurrences of claims within text (e.g., text 202), which may be regarded as a sentence labeling task. For example, in some instances, the claim detection module 110 comprises or is based on a natural language processing (NLP) model that is configured to analyze the parts of speech and/or other content of a body of text to detect particular language and/or context associated with claims or assertions.

In some implementations, the claim detection module 110 is initially or further trained using tagged training data under a full supervision or weak supervision training approach. For instance, the tagged training data may include domain-specific or enterprise-specific textual content that includes tags that indicate claims represented in the textual content. By way of illustrative example, many pharmaceutical companies include citations to relevant evidence on all claims or assertions made in pharmaceutical advertisements. Furthermore, during the review process for generating an advertisement, claims present within an advertisement that lack an evidentiary citation typically become flagged to allow for subsequent citation to supporting evidence or for removal of the claim from the advertisement. Thus, text from such advertisements that is associated with a citation to evidence or with a flag indicating a need for a citation may be regarded as text that includes a claim, and such text may therefore be used as training input for training a claim detection module 110 in an at least partially supervised manner. Aside from the pharmaceutical advertisement context, similar training input for identifying claims using citation or reference schemes may be obtained for other domains or enterprises using other domain-specific or enterprise-specific data.

Aside from citations, other artifacts that may be used to train a claim detection module 110 may include textual content following a heading or label within a paper, document, or publication. For example, many formal documents include headings indicating whether the text that follows the heading corresponds to a result, conclusion, objective, conclusion, or assertion. Thus, textual content following a heading or label associated with a "claim", "assertion", or related term may additionally or alternatively be used as training data for training a claim detection module 110.

Accordingly, a claim detection module 110 may be trained or configured to analyze the content and context of input text in a deep manner, enabling the recognition of claims within the input text. One will appreciate, in view of the present disclosure, that a claim detection module 110 may operate in a cross-domain or multi-domain manner or be tailored to specific technical fields, industries, enterprises, or even types of claims. In some instances, the operation of a claim detection module 110 is selectively modifiable by a user. For example, a user may provide user input specifying one or more types of claims the claim detection module 110 will detect within a body of text (e.g., claims related to particular subject matter). Multiple claim detection modules 110 may exist within a single system for use in different contexts.

FIG. 2A conceptually represents inputting the text 202 into the claim detection module 110 to detect one or more claims within the text 202. FIG. 2B illustrates an example of claims 204 detected by the claim detection module 110 in response to receiving the text 202 as input. The claims 204 are represented in FIG. 2B as underlined portions of the text 202. In the example shown in FIG. 2B, the portions of the text underlined in solid lines correspond to conclusory portions of the claims, whereas the portions of the text underlined in dotted lines correspond to contextual portions related to the conclusory portions.

Thus, in some instances, systems of the present disclosure are configured to emphasize one or more portions of the textual content determined by the claim detection module 110 to be contextually associated with the one or more claims. This may allow users to readily ascertain detected claims within text and correct any claim detection errors committed by the claim detection module 110.

For example, as shown in the left-hand portion of FIG. 2B, the claim detection module 110 has detected that the text 202 includes claims that tobacco smoking accounts for about 87% of lung cancer cases, that lung cancer is known to induce KRAS mutations, and that KRAS mutations induce expression of IL-6 in lung epithelium (e.g., as indicated by the solid and dotted underlining). The text 202 on the left-hand portion of FIG. 2B also shows, via underlining, claims detected in the latter portion of the text 202 that states, "IL-6 does not promote lung cancer proliferation and migration through STAT3 signaling." However, the left-hand side of FIG. 2B illustrates this latter portion of the text 202 as failing to mark the word "not" as contextually relevant to the detected claims (e.g., the word "not" omits dotted underlining showing its contextual relatedness to detected claims). Thus, in the example shown, the claim detection module 110 has initially failed to accurately detect the claims in the aforementioned latter portion of the text 202 represented in the left-hand portion of FIG. 2B by failing to implement the negative term "not" into the detected claims. Instead, the claim detection module 110 detected claims that IL-6 does promote lung cancer proliferation and migration through STAT3 signaling.

In some implementations, systems of the present disclosure receive user input making corrections to claim detection output provided by a claim detection module 110. Furthermore, in some implementations, such corrections are used to further refine and tune the claim detection module 110 to improve future performance in claim detection. Any form of user input is contemplated by the present disclosure, such as mouse click input, touch screen input, keyboard input, and/or others.

For example, FIG. 2B illustrates user input 206 directed to the term "not" in the latter portion of the text 202 represented in the left-hand portion of FIG. 2B. In the right-hand portion of FIG. 2B, text 202 is shown as including dotted underlining under the term "not" in the latter portion of the text, showing its contextual relevance to detected claims. Thus, in the example shown, the user input 206 operates to modify the portions of the text 202 that are interpreted by the claim detection module 110 as being relevant for claim detection by adding the negative term "not" as a part of the claims. Accordingly, responsive to the user input 206, the claim detection module 110 may redetermine the claims present within the text 202, which may cause presentation of modified claims 208. The modified claims 208 are represented via solid and dotted underlining in the right-hand side of FIG. 2B. For example, by inclusion of the negative term "not", the latter portion of the text 202 shown on the right-hand side of FIG. 2B includes depictions of claims that IL-6 does not promote lung cancer proliferation and migration through STAT3 signaling.

In some instances, as noted above, systems of the present disclosure are configured to respond to user input modifying portions of text determined to be part of claims by refining the claim detection module 110 to improve future claim detection performance. Accordingly, FIG. 2B also shows the modified claims 208 being utilized as training input 210, which may be used to further refine the claim detection module 110 (e.g., by reducing the likelihood that the claim detection module 110 will fail to omit the negative term "not" in subsequent claim detection processing).

Although FIG. 2B focuses on an example of user input 206 adding a term to modify detected claims, one will appreciate, in view of the present disclosure, that systems of the present disclosure may be configured to receive user input effectuating other types of modifications to detected claims and use such input to form training input for refining a claim detection module 110. For example, user input may remove terms from a detected claim, remove an entire claim that was detected in error (e.g., where emphasized text does not correspond to a claim), add an entire new claim that the claim detection module failed to detect, etcetera.

Figure 3:
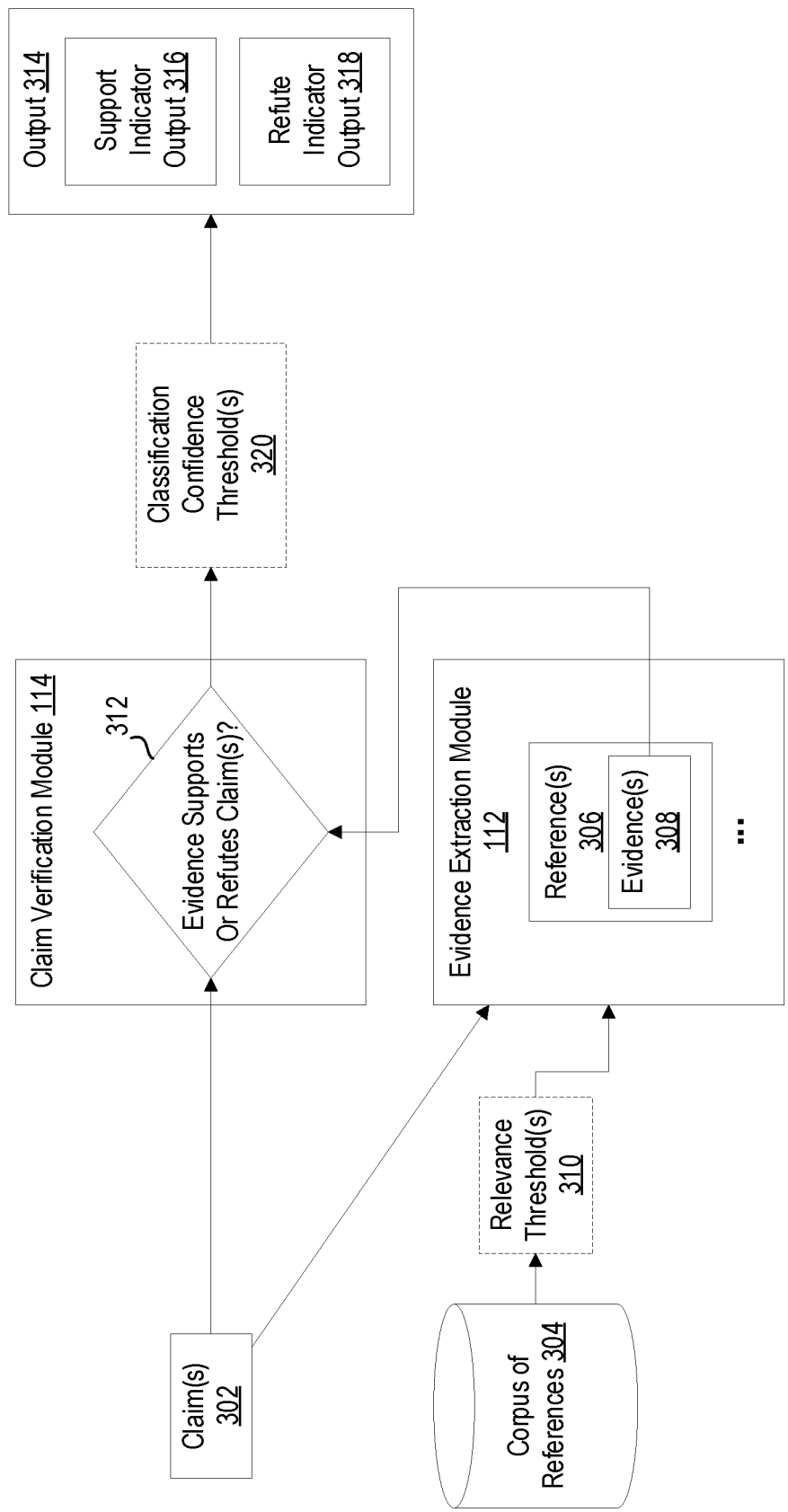
FIG. 3 illustrates a conceptual representation of extracting evidence from a corpus of references using an evidence extraction module and verifying detected claims using a claim verification module.

FIG. 3 illustrates a conceptual representation of extracting evidence from a corpus of references 304 using an evidence extraction module 112 and verifying detected claims using a claim verification module 114. In particular, FIG. 3 illustrates claim(s) 302, which may correspond to the claims 204 or the modified claims 208 according to the example shown and described with reference to FIGS. 2A and 2B, or any other claim(s) detected using a claim detection module 110. FIG. 3 also shows that the claim(s) 302 may be provided as input to an evidence extraction module 112. In some instances, a system accesses the evidence extraction module 112 and provides claim(s) 302 as input thereto automatically in response to detecting the claim(s) 302 within a body of text.

The corpus of references 304 may comprise any set or collection of documents, papers, publications, and/or other works that comprise evidence available for determining whether claim(s) 302 are supported by evidence, refuted by evidence, both supported and refuted by evidence, or neither supported nor refuted by evidence. The corpus of references may be stored within the system and/or one or more remote systems.

As used herein, "evidence" refers to any portion of a document, publication, paper, or other reference (e.g., within the corpus of references 304) that tends to prove or disprove the truth of a detected claim. In some instances, a corpus of references 304 includes is tailored to one or more particular domains (e.g., biological sciences, news, financial news, etc.) and/or particular entities (e.g., comprising documents or artifacts generated by one or more business entities). In other instances, the corpus of references 304 includes an index of content accessible via the internet. A corpus of references 304 may be stored and accessible in any form or format, without limitation.

In some implementations, the evidence extraction module 112 is trained using a set of ground truth data to enable the evidence extraction module 112 to identify references from the corpus of references 304 that include content that is related to claims detected via a claim detection module 110 (e.g., claim(s) 302). The set of ground truth data used to train the evidence extraction module 112 may be different from or at least partially overlap with the set of ground truth data used to train the claim detection module 110. In some instances, the evidence extraction module 112 is implemented as a recall model or retrieval model configured to search through the corpus of references 304 in a lightweight and rapid manner for pieces of evidence that are relevant to one or more detected claims (e.g., claim(s) 302). For example, the evidence extraction module 112 may operate in a term-based or token-based manner, such as by determining overlap between terms or entities associated with a detected claim and terms or entities associated with one or more references of the corpus of references 304 (e.g., via determining a vector dot product). In some instances, the evidence extraction module 112 utilizes embedding-based retrieval (e.g., by analyzing semantic relevance between words) or a combination of embedding-based and term-based retrieval.

In some implementations, the evidence extraction module 112 is initially or further trained using tagged training data under a full supervision or weak supervision training approach. For instance, the tagged training data may include domain-specific or enterprise-specific textual content that includes tags that link claims to relevant evidence. By way of illustrative example, many pharmaceutical companies maintain a corpus of documents or artifacts produced by the pharmaceutical company. Often, for a drug or project developed by a pharmaceutical company, a library of references is developed and maintained that includes tagging of evidence supporting claims made about the drug or project (e.g., claims made within advertisements or promotional materials for the drug or project). Such libraries may therefore provide a way of linking claims to relevant evidence and may therefore be used as training input for training an evidence extraction module 112 in an at least partially supervised manner. Aside from the pharmaceutical advertisement context, similar training input identifying evidence related to a claim may be obtained for other domains or enterprises using other domain-specific or enterprise-specific data.

Furthermore, many artifacts that are not necessarily domain-specific or enterprise-specific may be used to form a weak supervision signal for training an evidence extraction module 112. For example, many research papers, legal documents, and/or other types of formal publications include citations associated with claims or assertions made within the paper, document, or publication. Such citations often refer to other documents that are relevant to the claims or assertions, thereby providing a link between claims and evidence that is relevant to the claims. Thus, citations represented within many papers, documents, and/or other types of formal publications may be used as training input for training an evidence extraction module 112 in an at least partially supervised manner.

Accordingly, in some implementations, an evidence extraction module 112 is trained or configured to identify reference(s) 306 and/or portions of references (e.g., evidence(s) 308) that include content that is relevant or related to one or more claims (e.g., claim(s) 302). One will appreciate, in view of the present disclosure, that an evidence extraction module 112 may operate in a cross-domain or multi-domain manner or be tailored to specific technical fields, industries, enterprises, or even types of evidence.

In some instances, an evidence extraction module 112 identifies reference(s) 306 or evidence(s) 308 from reference(s) 306 as being relevant to a detected claim (e.g., claim(s) 302) by calculating a relevance score for the reference or piece of evidence and determining that the calculated relevance score satisfies relevance threshold(s) 310 (e.g., a threshold relevance score). A relevance score may take on various forms, such as a vector dot product value or any numerical value configured to represent semantic overlap between terms of a claim and terms of a reference or piece of evidence within a reference. The evidence extraction module 112 may refrain from obtaining or selecting references or pieces of evidence from a corpus of references 304 that fail to satisfy the relevance threshold(s) 310.

Furthermore, in some instances, a relevance score is modified by one or more attributes or characteristics of a reference or piece of evidence. For example, a reference may have a reputability score or veracity score (described in more detail hereinbelow) associated therewith, and a relevance score of a piece of evidence from the reference may be mathematically combined with the reputability or veracity score to provide a modified relevance score used to determine relevance of the piece of evidence to a particular claim.

Relevance threshold(s) 310 may comprise a particular relevance score that a reference or piece of evidence within a reference must satisfy to be determined by the evidence extraction module 112 to be relevant to a particular claim. In some instances, relevance threshold(s) 310 used by the evidence extraction module 112 is/are selectively modifiable by a user (e.g., via user input), allowing users to modify the breadth or focus of the reference(s) 306 and/or evidence(s) 308 identified by the evidence extraction module 112 as being relevant to the particular claim (e.g., claim(s) 302). The ellipsis within the evidence extraction module 112 as represented in FIG. 3 indicates that an evidence extraction module 112 may determine that any number of references(s) 306 or evidence(s) 308 is/are relevant to claim(s) 302.

In some instances, the operation of an evidence extraction module 112 is selectively modifiable by a user. For example, a user may provide user input specifying one or more types of references and/or evidence that the evidence extraction module 112 will search for within the corpus of references 304 (e.g., references that the user finds reputable or desirable, references that satisfy a veracity score threshold (as described hereinafter)). For instance, a user may specify particular fields of study, standards, bodies, publications, journals, etc. for the evidence extraction module 112 to search for within the corpus of references 304.

As another example, a user may specify a number of references and/or pieces of evidence that the evidence extraction module 112 will obtain from the corpus of references 304 for further analysis via the claim verification module 114, as will be described in more detail hereinbelow. Multiple claim detection modules 110 may exist within a single system for use in different contexts.

FIG. 3 conceptually represents the claim verification module 114 in association with a decision block 312 and shows a line extending from the claim(s) 302 toward the decision block 312 and from the evidence(s) 308 toward the decision block 312. The decision block 312 includes determining whether "evidence supports or refutes claim(s)", indicating that, in some implementations, the claim verification module 114 is trained to determine whether content of a reference (e.g., evidence(s) 308 of reference(s) 306 obtained from the corpus of references 304 via the evidence extraction module 112) supports or refutes a claim (e.g., claim(s) 302).

In some implementations, the claim verification module 114 is trained using a set of ground truth data to enable the claim verification module 114 to determine whether evidence supports or refutes a claim. The set of ground truth data used to train the claim verification module 114 may be different from or at least partially overlap with the set of ground truth data used to train the claim detection module 110 and/or the set of ground truth data used to train the evidence extraction module 112.

In some instances, the claim verification module 114 comprises or is based on an NLP model that is configured to analyze the parts of speech and/or other content of a body of text to detect particular language and/or context associated with claims or assertions. For example, in some implementations, a claim verification module 114 is configured to analyze context of a claim and context of evidence to determine similarity or dissimilarity therebetween (e.g., whether the content of the claim and the content of the evidence are associated with similar or dissimilar conclusions, or whether the content of the evidence substantiates the content of the claim).

In some implementations, the claim verification module 114 is initially or further trained using tagged training data under a full supervision or weak supervision training approach. For instance, the tagged training data may include domain-specific or enterprise-specific textual content that includes tags that indicate that a reference or piece of evidence supports or refutes one or more particular claims. For example, as indicated hereinabove, pharmaceutical companies often maintain libraries of references and pieces of evidence within references that are flagged as supporting claims made in advertising materials. Thus, libraries associating claims with supporting evidence may therefore be used as training input for training a claim verification module 114 in an at least partially supervised manner.

Furthermore, as noted above, the creation of pharmaceutical advertisements often entails a review process whereby reviewers are able to flag improper claims. Such flags may include flagging of claims for which cited evidence fails to support the claim or actually refutes the claim. Thus, such flagging data may be used as training input for training a claim verification module 114 in an at least partially supervised manner. Aside from the pharmaceutical advertisement context, similar training input indicating whether evidence supports a claim may be obtained for other domains or enterprises using other domain-specific or enterprise-specific data.

Furthermore, many artifacts that are not necessarily domain-specific or enterprise-specific may be used to form a weak supervision signal for training a claim verification module 114. For example, as noted above, many research papers, legal documents, and/or other types of formal publications include citations associated with claims or assertions made within the paper, document, or publication. Such citations often refer to other documents or portions of documents that support or refute the claims or assertions associated therewith (e.g., in adversarial or persuasive writing, research publications, reports, etc.). Thus, citations associated with claims or assertions as represented within many papers, documents, and/or other types of formal publications may provide an indication of whether references or evidence represented in citations support or refute claims associated with the citations. Accordingly, citations and/or claims represented within many papers, documents, and/or other types of formal publications may be used as training input for training a claim verification module 114 in an at least partially supervised manner.

Accordingly, in some implementations, a claim verification module 114 is trained or configured to determine whether evidence(s) 308 support or refute claims 302 based on a deep contextual understanding of the claims 302 and the evidence(s) 308. One will appreciate, in view of the present disclosure, that a claim verification module 114 may operate in a cross-domain or multi-domain manner or be tailored to specific technical fields, industries, enterprises, or even types of claims and/or evidence.

In this regard, a claim verification module 114 is configurable to determine a set of references or pieces of evidence that support or refute the claim(s) 302 (a set may contain one or more elements). FIG. 3 furthermore illustrates that, in some implementations, a system is configured to generate output 314 based on a determination of a set of references or pieces of evidence that support or refute the claim(s) 302. The output 314 may include support indicator output 316 (e.g., where the set of references or pieces of evidence supports a claim) and/or refute indicator output 318 (e.g., where the set of references or pieces of evidence refutes a claim). The support indicator output 316 visually indicates (e.g., on a user interface) that the claim(s) 302 are supported by evidence, and the refute indicator output 318 visually indicates (e.g., on a user interface) that the claim(s) 302 are refuted by evidence. Additional details concerning support indicators and refute indicators will be provided hereinafter.

One will appreciate, in view of the present disclosure, that a claim verification module 114 may determine multiple sets of references or pieces of evidence (e.g., a set of supporting references or pieces of evidence and a set of refuting references or pieces of evidence) and that a set of references or pieces of evidence may comprise evidence that supports a claim as well as evidence that refutes a claim.

In some implementations, the claim verification module 114 associates a classification confidence score with its determination as to whether evidence supports or refutes a claim. The classification confidence score may numerically represent an amount of confidence in a label assigned to a piece of evidence vis-à-vis a claim (e.g., a label of whether the piece of evidence supports the claim or refutes the claim). In some instances, the classification confidence score is based on an error or loss metric or is based on a similarity or dissimilarity of context and/or conclusion between the claim and the evidence (e.g., represented as a percentage).

Furthermore, in some implementations, a system is configured to omit one or more references or pieces of evidence from the set(s) of references determined by the claim verification module 114 to support or refute a claim where the one or more references or pieces of evidence fail to satisfy classification confidence threshold(s) 320. The classification confidence threshold(s) 320 may comprise a particular classification confidence score (e.g., 50% or greater) that a reference or piece of evidence must satisfy to be determined by the claim verification module 114 to support or refute a claim. In some instances, the classification confidence threshold(s) 320 is/are modifiable by a user (e.g., via user input), allowing users to modify the breadth or focus of the references or evidence determined by the claim verification module 114 to support or refute claims.

Figure 4:
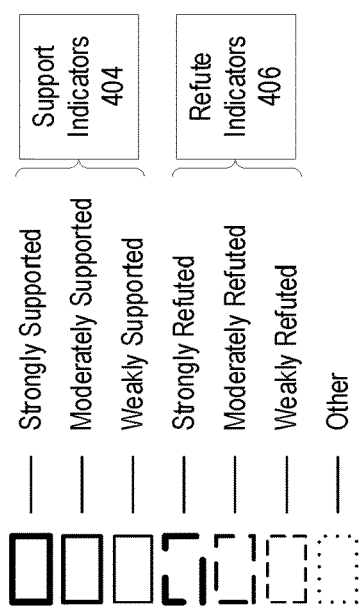
FIG. 4 illustrates an example user interface that includes support indicators and refute indicators associated with a body of text.

FIG. 4 illustrates an example user interface 400 that includes support indicators 404 and refute indicators 406 associated with text 202. FIG. 4 illustrates that the output 314 discussed above with reference to FIG. 3 may comprise or cause the presentation of one or more support indicators 404 and/or one or more refute indicators 406 within a user interface 400 and in association with claims represented in the text 202 (e.g., claims identified or detected for verification as described above).

FIG. 4 depicts the support indicators 404 as solid rectangles and illustrates the refute indicators 406 as dashed rectangles. FIG. 4 also illustrates that support indicators 404 and refute indicators 406 may take on various forms to indicate a weight of support or a weight of refutation for analyzed claims. For instance, FIG. 4 shows an example in which the support indicators 404 include a first type with a thick linewidth indicating that a claim is strongly supported, a second type with a moderate linewidth indicating that a claim is moderately supported, and a third type with a thin linewidth indicating that a claim is weakly supported. Similarly, FIG. 4 shows an example in which the refute indicators 406 include a first type with a thick linewidth indicating that a claim is strongly refuted, a second type with a moderate linewidth indicating that a claim is moderately refuted, and a third type with a thin linewidth indicating that a claim is weakly refuted.

The example depicted in FIG. 4 shows that the claim that tobacco smoking accounts for about 87% of lung cancer cases is strongly supported by evidence represented within the corpus of references 304 (e.g., as determined using the evidence extraction module 112 and the claim verification module 114). The example of FIG. 4 also shows that the claim that lung cancer induces KRAS mutations is weakly supported by evidence and that KRAS mutations in turn induce expression of IL-6 in lung epithelium is moderately supported by evidence. Furthermore, the example of FIG. 4 shows that the claim that IL-6 does not promote lung cancer proliferation is strongly refuted by evidence (e.g., as determined using the evidence extraction module 112 and the claim verification module 114).

In this way, a user interacting with the user interface may become informed as to the veracity of the claims represented within the text 202 (relative to a corpus of references 304), whether or not the user generated the text 202 and potentially in real-time.

FIG. 4 also illustrates an example additional indicator represented as a dotted rectangle and classified as "other", which may have different uses in different implementations. For example, in some implementations, the additional indicator indicates that a claim is both supported and refuted by evidence with similar weight, or that a claim is neither supported nor refuted by evidence (relative to a corpus of references). In some instances, an additional indicator may comprise a combination of a support indicator 404 and a refute indicator 406. The example of FIG. 4 places an additional indicator on the claim that IL-6 does not promote lung cancer migration through STAT3 signaling, indicating that the claim is both supported and refuted by evidence or that the claim is neither supported nor refuted by evidence.

The example shown in FIG. 4 is illustrative only and non-limiting, and support indicators 404 and refute indicators 406 may be embodied in other ways (e.g., using different colors or shades to depict support or refutation or weights thereof). Furthermore, in some instances, the support indicators 404 and/or the refute indicators 406 do not indicate a weight of support or a weight of refutation for associated claims.

FIGS. 5, 6, 7, and 8 illustrate examples of detecting user input directed at a support indicator and examples of actions that may be performed and/or content that may be displayed in response to the user input.

Figure 5:
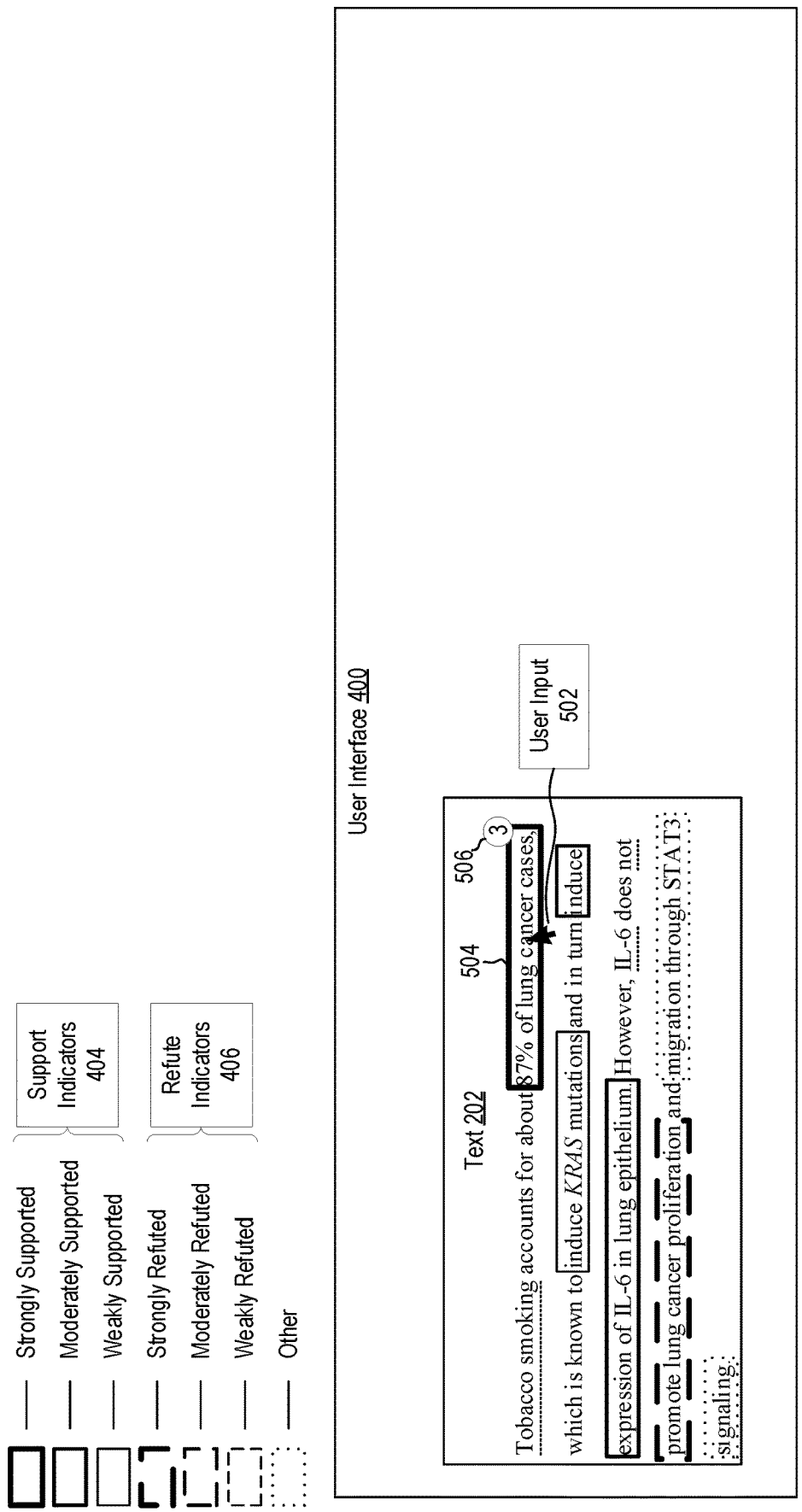
FIGS. 5, 6, 7, and 8 illustrate examples of detecting user input directed at a support indicator and examples of actions that may be performed and/or content that may be displayed in response to the user input.

FIG. 5 illustrates user input 502 directed to the support indicator 504 associated with the claim that tobacco smoking accounts for about 87% of lung cancer cases, as represented within the text 202 of the user interface 400. As indicated above, the user input 502 may take on various forms (e.g., hover input, selection input via clicking or tapping, voice or gesture input, etc.). FIG. 5 shows an example in which a system is configured to display a number of references 506 that support a claim in response to the user input 502 directed to the support indicator 504 associated with the claim. The number of references 506 may comprise an additional or alternative indication of the weight of support for the claim.

It should be noted that different or additional numbers, such as a number of pieces of evidence that support a claim, may be displayed for a claim in response to user input directed to the claim or to a support indicator associated with the claim (or automatically).

Figure 6:
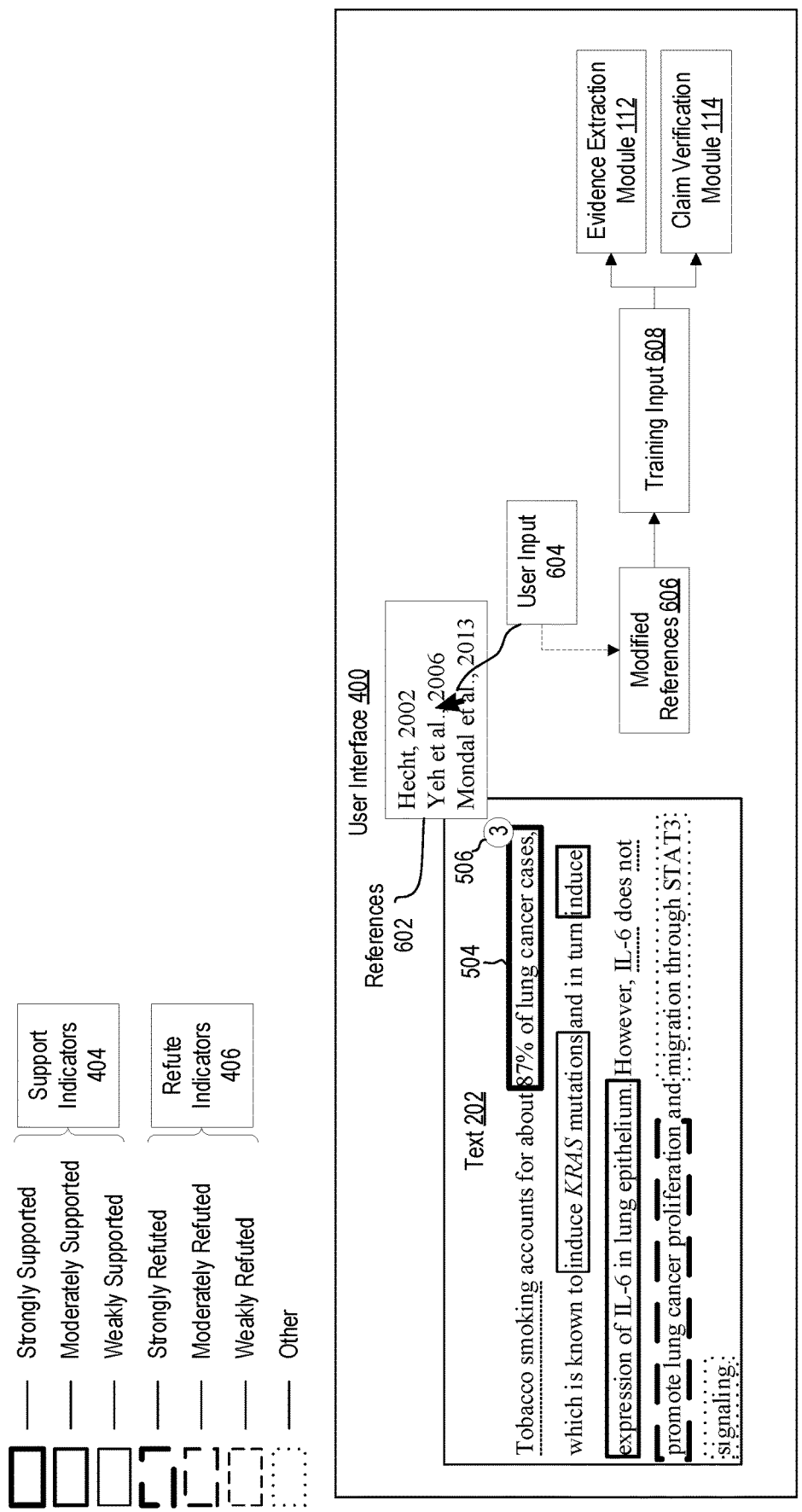

FIG. 6 illustrates a representation of references 602 being displayed within the user interface 400 in association with the support indicator 504 (or in association with the claim or displayed number of references 506 associated with the support indicator 504). The references 602 may comprise one or more references of a set of references determined by the claim verification module 114 to support the claim that tobacco smoking accounts for 87% of lung cancer cases. As shown in FIG. 6, the references 602 include Hecht, 2002; Yeh et al., 2006; and Mondal et al., 2013. The presentation of the references 602 may be triggered in response to user input directed to the support indicator 504, the claim underlying the support indicator 504, the number of references 506, or others.

The presentation of the references 602 may allow users to readily perceive and/or interact with the references determined by the claim verification module 114 to be supportive of the underlying claim. For example, in some implementations, the references 602 may include link functionality, allowing users to quickly navigate to one or more of the references 602 for further analysis or review or other purposes. As another example, the references 602 may be selectable to trigger generation and/or updating of a bibliography or other compilation of references, which may assist users in formal writing (in some instances, a bibliography or other compilation of references is automatically generated during document authoring).

FIG. 6 also illustrates an example of user input 604 modifying the references 602 determined by the claim verification module 114 to support the underlying claim. In particular, the user input 604 shown in FIG. 6 is directed to a particular reference of the references 602 (i.e., Yeh et al.). For example, a user may determine that Yeh et al. fails to support the claim that tobacco smoking accounts for about 87% of lung cancer cases, in contrast to the determination of the claim verification module 114 and/or the evidence extraction module 112 (e.g., Yeh et al. may actually refute such a claim or may be irrelevant to such a claim). Accordingly, the user input 604 may be operable to indicate that Yeh et al. fails to support the underlying claim, such as by removing Yeh et al. from the representation of the references 602 or by other user control input (e.g., indicating that Yeh et al. is irrelevant to the underlying claim). Thus, FIG. 6 shows that the user input 604 provides modified references 606 (e.g., omitting Yeh et al.). The removal of Yeh et al. and/or the modified references 606 may be utilized as training input 608 to further train or refine the evidence extraction module 112 and/or the claim verification module 114 (e.g., to reduce the likelihood of the inclusion of irrelevant evidence by the evidence extraction module 112 and/or to reduce the likelihood of improper evidence classification by the claim verification module 114).

Figure 7:
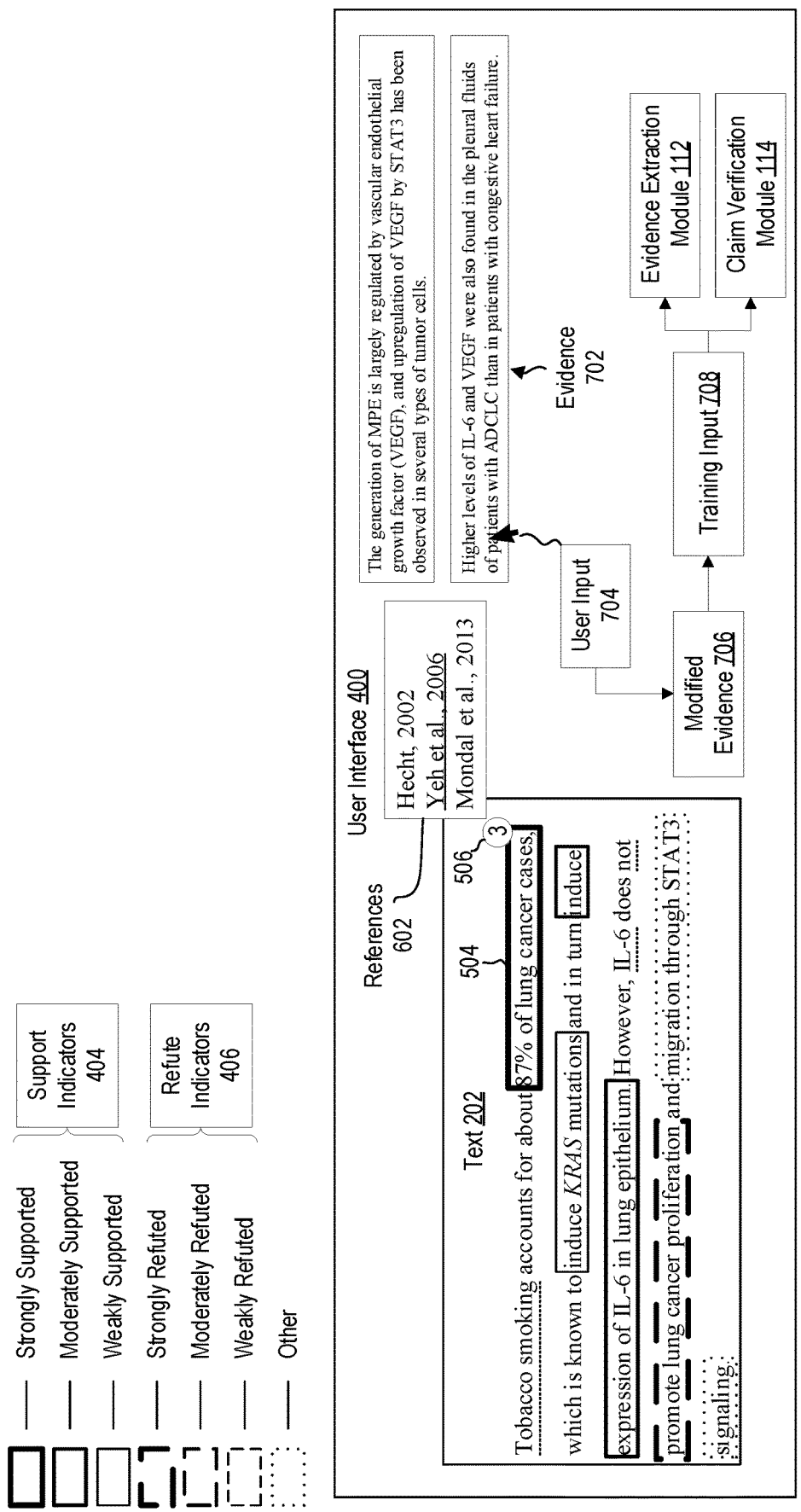

FIG. 7 illustrates a representation of evidence 702 being displayed within the user interface 400 in association with the references 602 (or in association with the underlying claim, the support indicator 504, the displayed number of references 506, etc.). As shown in FIG. 7, the evidence 702 may comprise one or more particular pieces of evidence from one or more of the references 602. For example, FIG. 7 illustrates the reference Yeh et al. as being underlined, indicating that the evidence 702 presented is from Yeh et al. The presentation of the evidence 702 may be triggered in response to user input directed to one or more of the references 602, the support indicator 504, the claim underlying the support indicator 504, the number of references 506, or others.

The presentation of the evidence 702 may allow users to readily perceive and/or interact with the evidence determined by the claim verification module 114 to be supportive of the underlying claim. For example, in some implementations, the evidence 702 may include link functionality, allowing users to quickly navigate to the evidence 702 for further analysis or review or other purposes. As another example, the evidence 702 may be selectable to trigger generation and/or updating of a bibliography or other compilation of references or evidence, which may assist users in formal writing.

FIG. 7 also illustrates an example of user input 704 modifying the evidence 702 determined by the claim verification module 114 to support the underlying claim. In particular, the user input 704 shown in FIG. 7 is directed to a particular piece of evidence from the evidence 702, which is a statement from Yeh et al. that "Higher levels of IL-6 and VEGF were also found in the pleural fluids of patients with ADCLC than in patients with congestive heart failure." By way of illustrative example, a user may determine that this statement from Yeh et al. fails to support the claim that tobacco smoking accounts for about 87% of lung cancer cases, contrary to the determination of the claim verification module 114 and/or the evidence extraction module 112 (e.g., a user may determine that a statement actually refutes such a claim or is irrelevant to such a claim).

Accordingly, the user input 704 may be operable to indicate that the statement from Yeh et al. referenced above fails to support the underlying claim, such as by removing the statement from the representation of the evidence 702 or by other user control input (e.g., indicating that the statement is irrelevant to the underlying claim). Thus, FIG. 7 shows that the user input 704 provides modified evidence 706 (e.g., omitting the aforementioned statement from Yeh et al.). The removal of the statement from Yeh et al. and/or the modified evidence 706 may be utilized as training input 708 to further train or refine the evidence extraction module 112 and/or the claim verification module 114 (e.g., to reduce the likelihood of the inclusion of irrelevant evidence by the evidence extraction module 112 and/or to reduce the likelihood of improper evidence classification by the claim verification module 114).

Although FIGS. 5, 6, and 7 focus, in at least some respects, on system functions (e.g., refining modules, presenting references and/or evidence) in response to user interactions directed to a support indicator or to a claim associated with a support indicator, one will appreciate, in view of the present disclosure, that the principles and system functions discussed with reference to FIGS. 5, 6, and 7 are applicable in response to user interactions directed to a refute indicator or to a claim associated with a refute indicator (or to other indicators). For example, user input directed to a refute indicator or a claim associated with a refute indicator may trigger the display of a number of references or evidence that refute the claim or the display of representations of references or evidence that refute the claim. As another example, user input indicating that a reference or piece of evidence purported by the claim verification module 114 and/or evidence extraction module 112 to refute a claim actually fails to refute a claim may trigger the refining of the evidence extraction module 112 and/or the claim verification module 114 based on correction.

Figure 8:
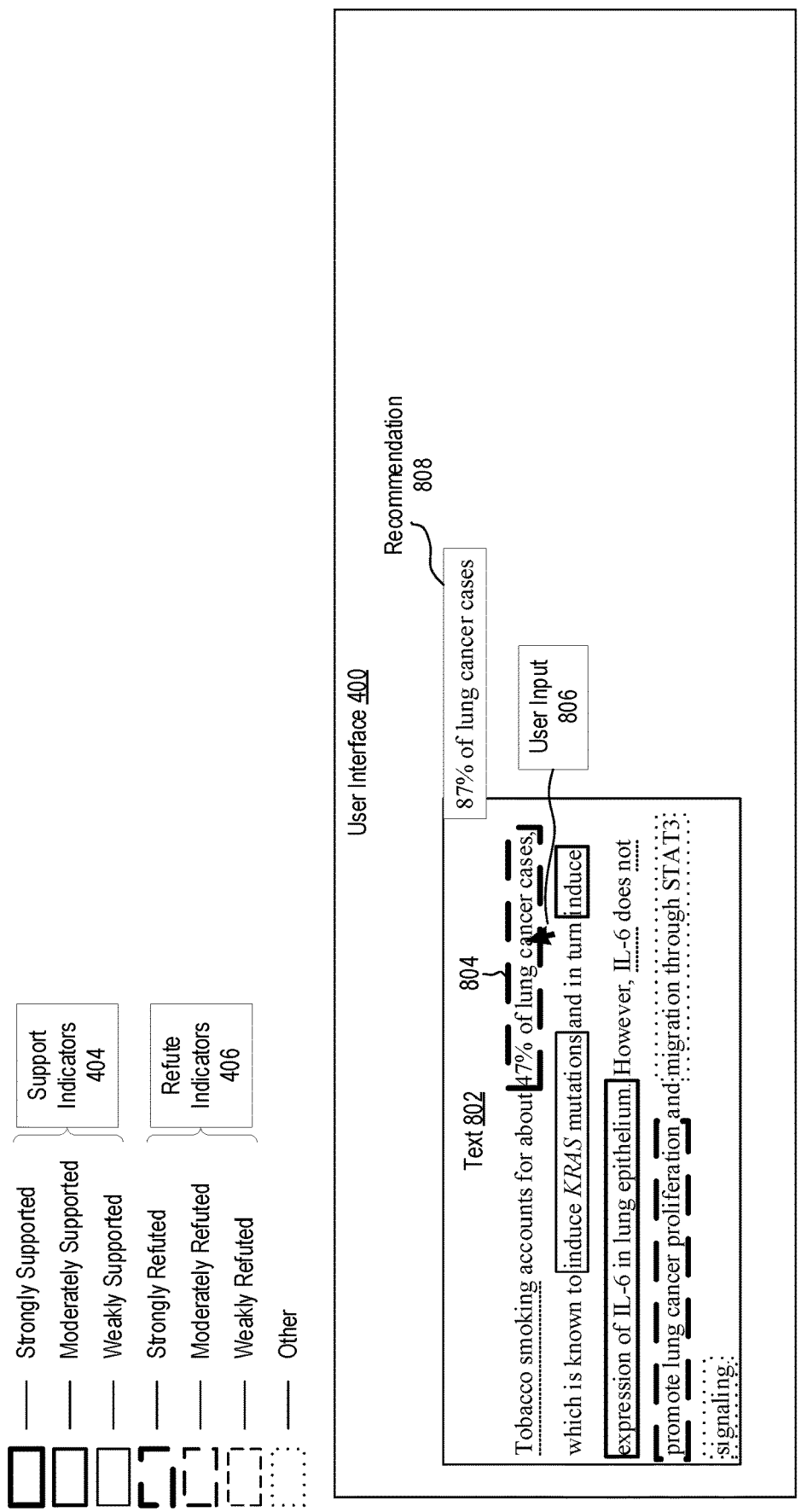

FIG. 8 illustrates text 802 that is different from the text 202 hitherto described. In particular, the text 802 states that tobacco smoking accounts for about 47% of lung cancer cases (in contrast with the text 202, which states that tobacco smoking accounts for about 87% of lung cancer cases). FIG. 8 illustrates a refute indicator 804 associated with the claim that tobacco smoking accounts for about 47% of lung cancer cases, indicating that the claim verification module 114 has determined that the claim is strongly refuted by evidence (e.g., refuted with high confidence).

FIG. 8 also shows user input 806 directed to the refute indicator 804 (or directed to the claim that underlies the refute indicator 804). In some implementations, as shown in FIG. 8, the user input 806 triggers the presentation of a recommendation 808 for modifying the claim associated with the refute indicator 804. In particular, the recommendation 808 comprises modifying the text "47% of lung cancer cases" to instead state "87% of lung cancer cases". A system may utilize a language model to facilitate text generation or modification to provide the recommendation 808 based on evidence from a set of relevant references (e.g., as determined by the evidence extraction module 112 and the claim verification module 114). Such functionality may facilitate rapid correction of claims or assertions that are refuted by evidence, which may improve user experiences. In some instances, recommendations are automatically implemented to modify text (e.g., within a document authoring context).

Figure 9:
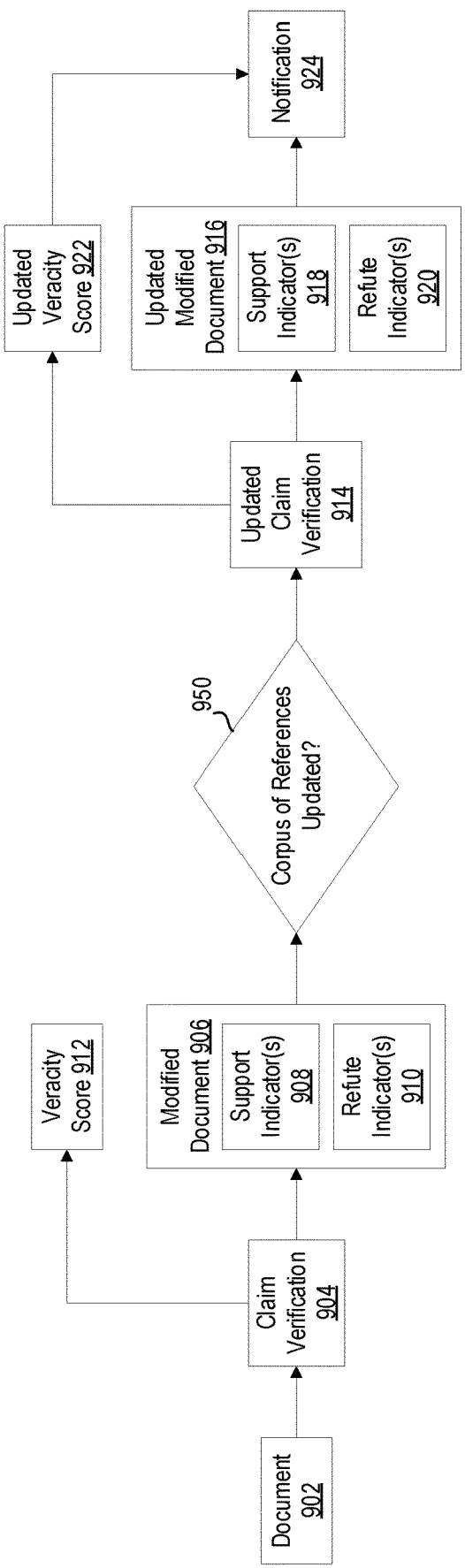
FIG. 9 illustrates a conceptual representation of performing claim verification on claims present in a document and performing updated claim verification in response to detecting an update to a corpus of references.

FIG. 9 illustrates a conceptual representation of performing claim verification on claims present in a document and performing updated claim verification in response to detecting an update to a corpus of references. In particular, FIG. 9 illustrates an example in which a system may receive or identify a document 902 that includes a body of text. The document may take on any suitable form without limitation. The system performs claim verification 904 on the body of text of the document 902 as described hereinabove (e.g., with reference to FIGS. 2A, 2B, 3, and 4). For example, claim verification 904 may include detecting claims within the document 902 using a claim detection module 110, automatically searching within a corpus of references for references and/or evidence related to the detected claims using an evidence extraction module 112, and determining whether the related references and/or evidence support or refute the detected claims.

Based on the claim verification 904, the system generates a modified document 906 that includes support indicator(s) 908 and/or refute indicator(s) 910, indicating whether the various claims present within the document 902 are, respectively, supported or refuted by evidence. The support indicator(s) 908 and/or the refute indicator(s) 910 may be included in the modified document in association with the claims verified according to the claim verification 904. Generating the modified document 906 may include making modifications to an existing document (e.g., within a document authoring context), creating a new document, etc.

FIG. 9 also illustrates that, in some instances, a system generates a veracity score 912 based on the claim verification 904. A veracity score 912 indicates a level of evidentiary support for claims present in the document 902 (or modified document 906). For example, in some instances, a veracity score is represented as a percentage of the claims present in the document 902 that are supported by evidence, which may be modified based on the weight of support for the claims, the presence and/or number of claims that are refuted by evidence (and/or the weight of refutation for the same), etc. In some instances, a veracity score may be included with a modified document 906 or presented on a user interface for viewing by a user (e.g., in a content browsing context).

FIG. 9 furthermore illustrates that, in some implementations, the system is configured to determine that the corpus of references used for the claim verification 904 has been updated (e.g., represented in FIG. 9 by decision block 950). An update to a corpus of reference may comprise any change to the references or evidence available to or within the corpus of references. For example, the system may detect that additional publications associated with journals of the corpus of references have been published. As another example, the system may detect that updates have been made to content of the corpus of references (e.g., updates to news articles). In yet another example, the system may detect that one or more references or pieces of evidence have been removed from the corpus of references (e.g., retraction of a publication). In still another example, the system may detect changes in reputability or veracity of documents of the corpus of references or of entities associated with generating documents of the corpus of references (e.g., where it arises that an author falsified published information). A system may check for updates to a corpus of references according to any temporal scheme (e.g., daily, weekly, hourly, etc.) and by any suitable means (e.g., crawlers, change detection processes).

As depicted in FIG. 9, in response to determining that the corpus of references has been updated, the system performs updated claim verification 914, which includes processes similar to those discussed above for claim verification 904 but with an updated corpus of references (e.g., using the evidence extraction module 112 to determine relevant references and/or evidence and using the claim verification module 114 to determine whether the relevant references and/or evidence supports or refutes detected claims). Based on the updated claim verification 914, the system generates an updated modified document 916 that includes updated support indicator(s) 918 and/or updated refute indicator(s) 920. For example, via the updated claim verification 914 using the updated corpus of references, the system may determine that additional or stronger evidence supports or refutes one or more of the claims within the document 902, which may be reflected in the updated support indicator(s) 918 and/or updated refute indicator(s) 920. As another example, the system may determine that a claim that was previously refuted by evidence has become supported by evidence in view of the updated claim verification 914, and this change may be reflected in the updated support indicator(s) 918 and/or updated refute indicator(s) 920.

Similarly, based on the updated claim verification 914, in some instances, the system generates an updated veracity score 922 to reflect changes in the support or refutation of the claims of the document 902 in view of the updates to the corpus of references.

FIG. 9 also shows that, in some implementations, the system generates a notification 924 based on the updated claim verification 914. In some instances, the notification 924 is generated for an entity associated with the document 902 (or the updated modified document 916), such as an entity responsible for authoring the document 902 or an entity interested in the progress of the document 902 (e.g., a user who has made one or more citations to the document 902 in other works). In some instances, the notification 924 is generated in response to the system detecting that the updated modified document 916 differs from the modified document 906 (e.g., by detecting differences between the support indicator(s) 908 and the updated support indicator(s) 918, between the refute indicator(s) 910 and the updated refute indicator(s) 920) or in response to detecting that the updated veracity score 922 differs from the veracity score 912. The notification may take on any form (e.g., a report that details the changes in evidentiary support and/or veracity score, a simple notification that a change in evidentiary support has occurred) and may be generated or transmitted to a particular entity in any suitable manner (e.g., via automated e-mail, surfacing a user interface presentation, etc.).

Figure 10:
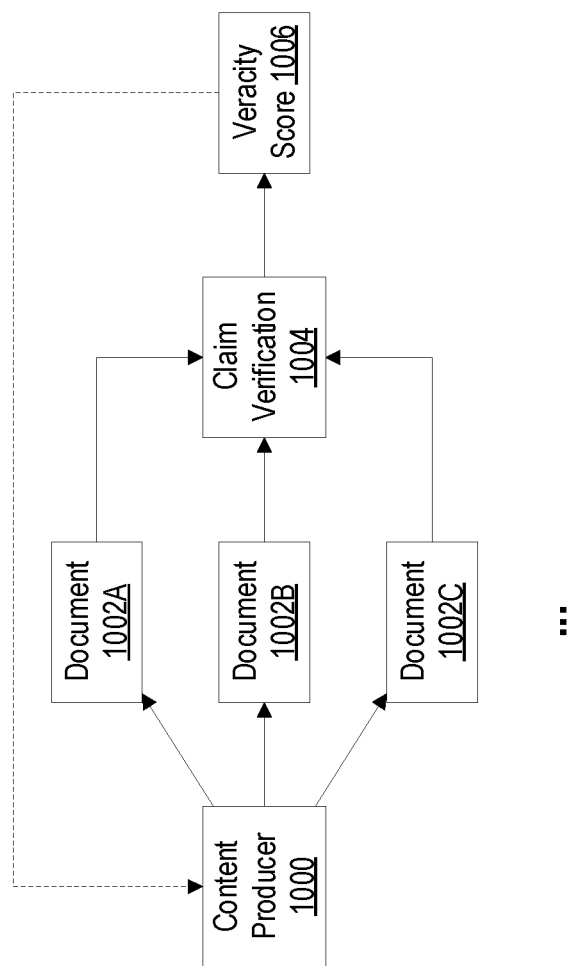
FIG. 10 illustrates a conceptual representation of generating a veracity score based on performing claim verification on one or more documents.

FIG. 10 illustrates a conceptual representation of generating a veracity score 1006 based on performing claim verification 1004 on one or more documents (1002A, 1002B, 1002C, etc.). As indicated previously, a veracity score (e.g., veracity score 1006) provides a level of evidentiary support for claims present in one or more documents and may be determined based on the performance of claim verification (e.g., claim verification 1004). In this regard, FIG. 10 conceptually represents a content producer 1000, which may include any entity associated with generating content that includes claims or assertions (e.g., an entity, organization, person, person within an entity or organization, etc.). FIG. 10 also illustrates documents 1002A, 1002B, 1002C, and/or others (indicated by the ellipsis) generated via the content producer 1000. In the example depicted in FIG. 10, a system detects claims present within such documents 1002A, 1002B, and 1002C and performs claim verification 1004 thereon to determine one or more sets of references and/or evidence that support or refute the claims present within the documents 1002A, 1002B, and 1002C (e.g., similar to claim verification 904 or updated claim verification 914 discussed above). Based on the claim verification 1004, the system generates a veracity score 1006 for the documents.

In the example shown in FIG. 10, the documents 1002A, 1002B, and 1002C are all created via the content producer 1000. Accordingly, the veracity score 1006 generated for the documents 1002A, 1002B, and 1002C may be associated with the content producer 1000 (illustrated in FIG. 10 by a dashed line extending from the veracity score 1006 to the content producer 1000) to indicate a tendency of the content producer 1000 to create content that is supported by evidence (or a tendency of the content producer 1000 to create content that is not supported by evidence). Such functionality may assist users in content consumption by providing users with a readily understandable metric for assessing the veracity of a content producer.

Example Method(s) for Facilitating Claim Verification

The following discussion now refers to a number of methods and method acts that may be performed by the disclosed systems. Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 11:
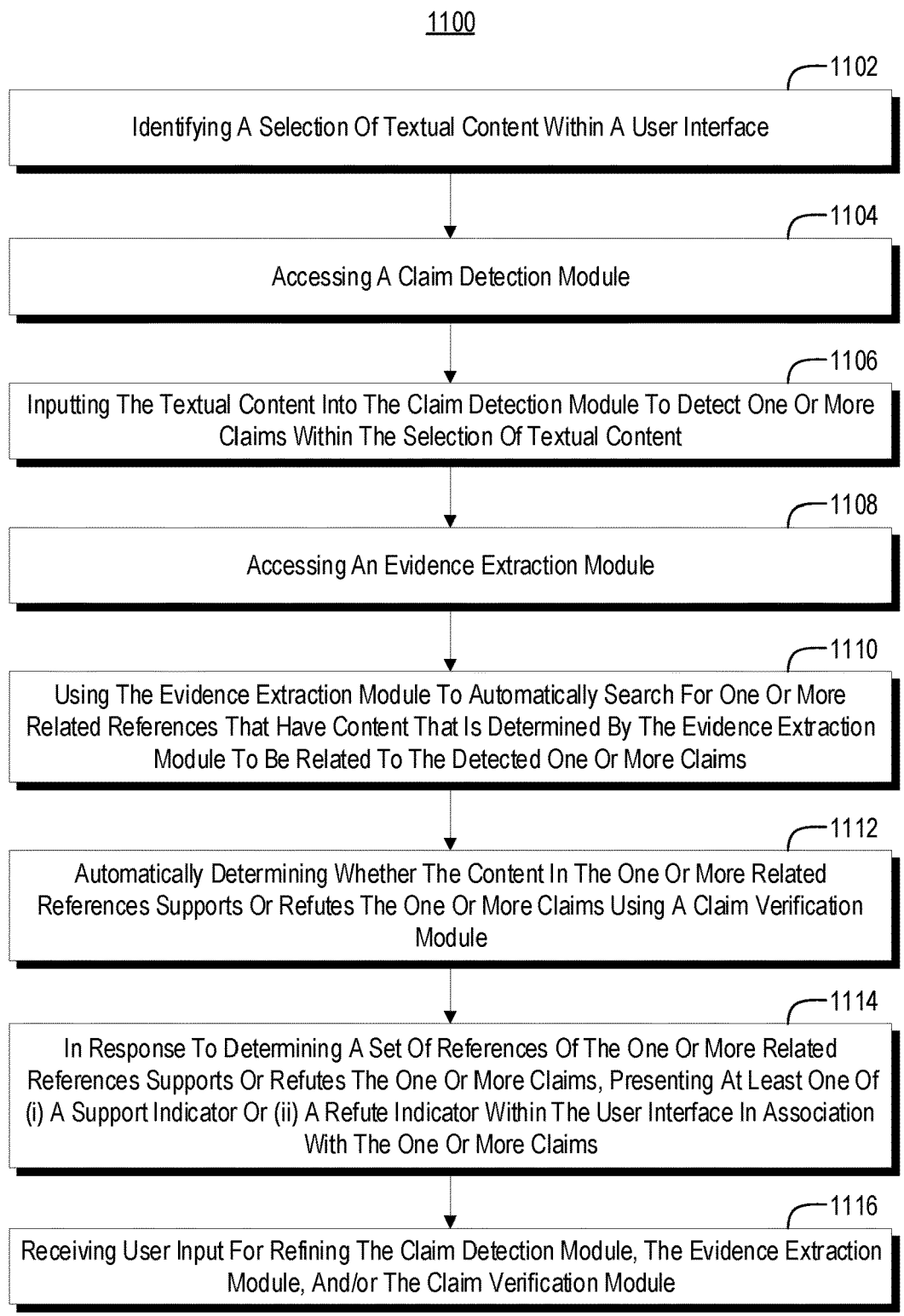
FIGS. 11, 12, and 13 illustrate example flow diagrams depicting acts associated with claim verification, in accordance with the present disclosure.
Figure 12:
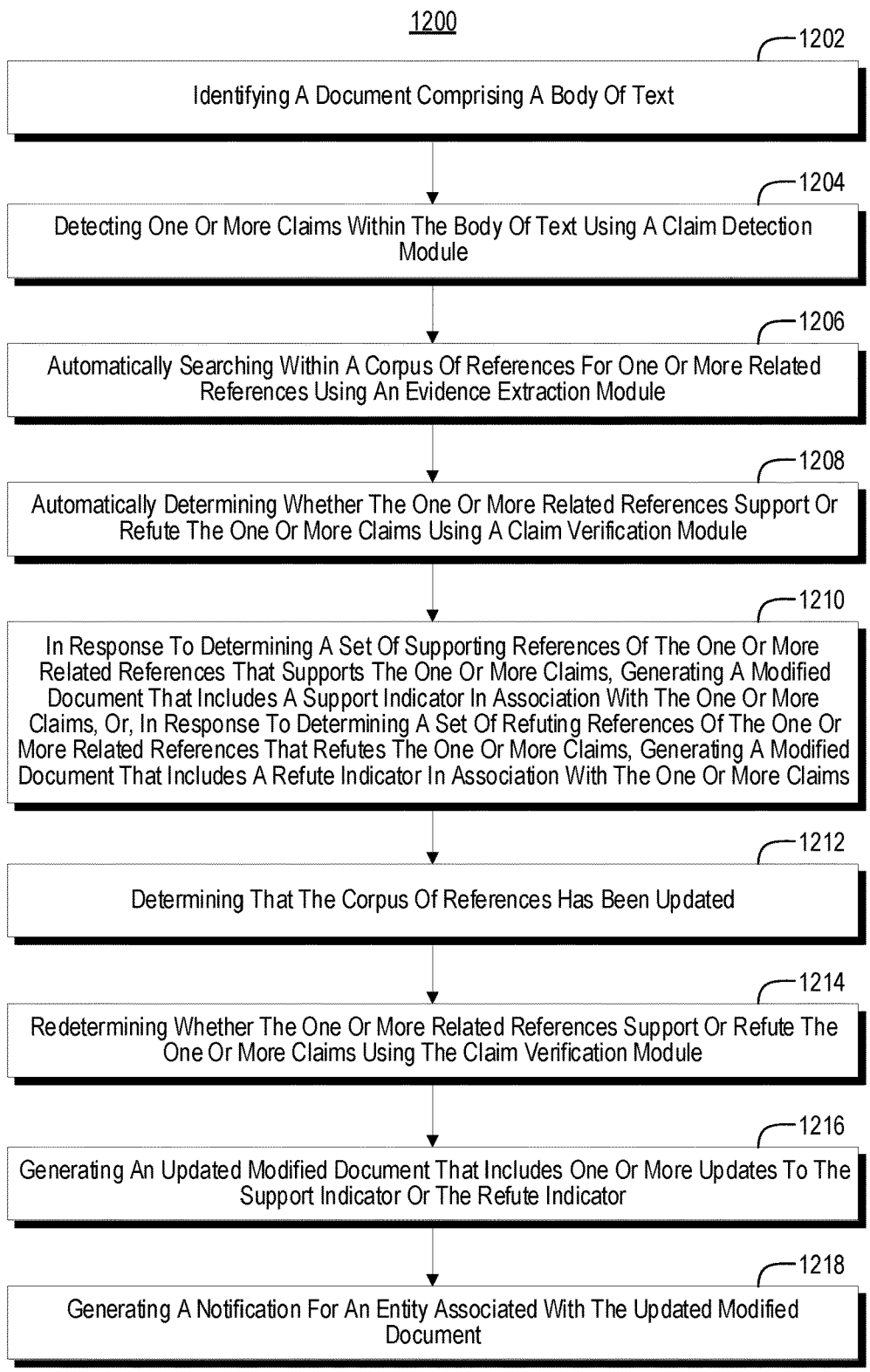
Figure 13:
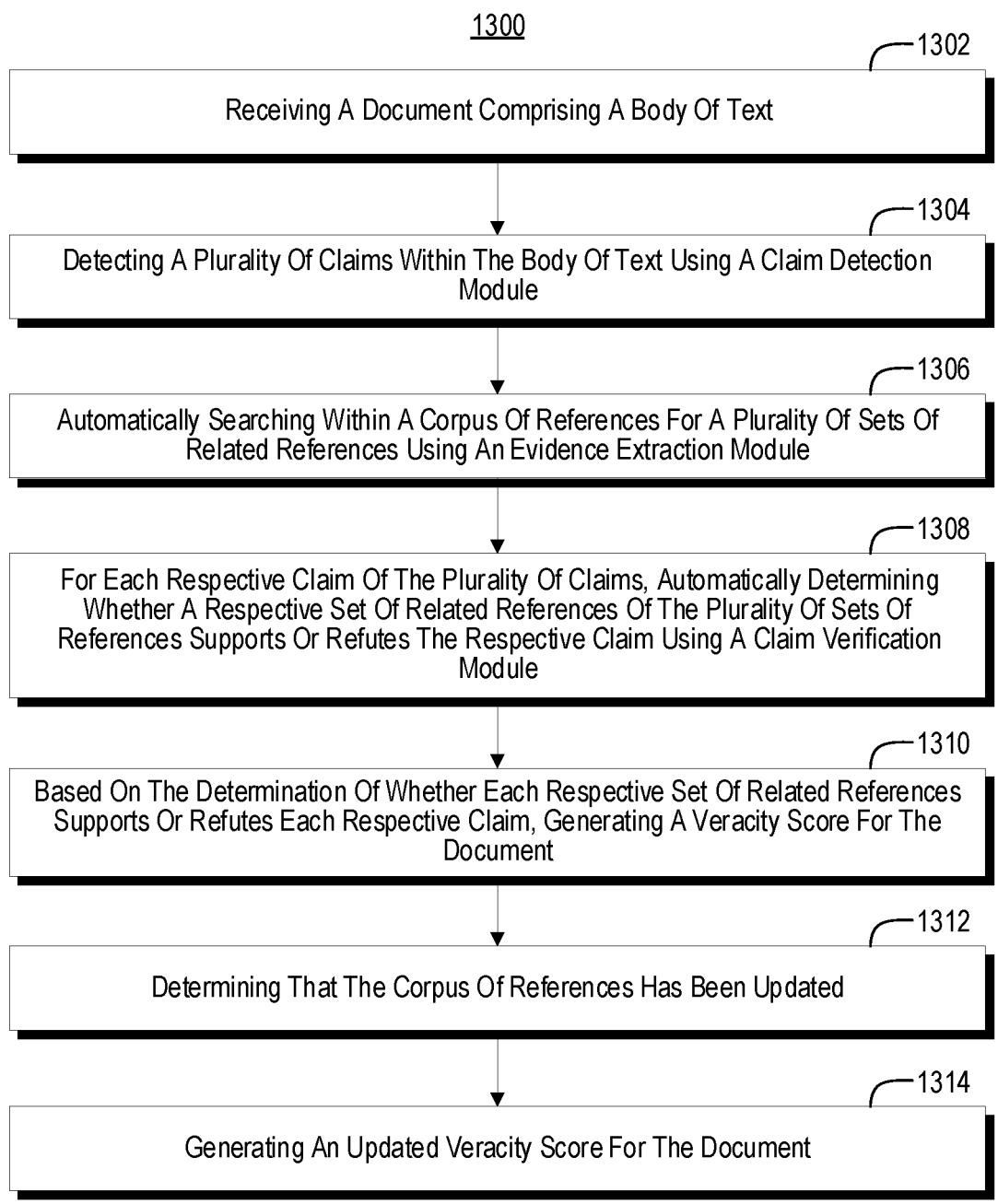

FIGS. 11, 12, and 13 illustrate example flow diagrams 1100, 1200, and 1300, respectively, depicting acts associated with claim verification, in accordance with the present disclosure. The discussion of the various acts represented in the flow diagrams include references to various hardware components described in more detail with reference to FIG. 1.

Act 1102 of flow diagram 1100 includes identifying a selection of textual content within a user interface. Act 1102 is performed, in some instances, by a system 100 utilizing processor(s) 102, storage 104, I/O system(s) 124, communication system(s) 126, and/or other components. The user interface and/or the textual content may take on various forms as described hereinabove.

Act 1104 of flow diagram 1100 includes accessing a claim detection module. Act 1104 is performed, in some instances, by a system 100 utilizing processor(s) 102, storage 104, I/O system(s) 124, communication system(s) 126, and/or other components. In some implementations, the claim detection module is trained with a first set of ground truth to enable the claim detection module to detect occurrences of claims within text.

Accordingly, act 1106 of flow diagram 1100 includes inputting the textual content into the claim detection module to detect one or more claims within the selection of textual content. Act 1106 is performed, in some instances, by a system 100 utilizing processor(s) 102, storage 104, claim detection module 110, I/O system(s) 124, communication system(s) 126, and/or other components.

Act 1108 of flow diagram 1100 includes accessing an evidence extraction module. Act 1108 is performed, in some instances, by a system 100 utilizing processor(s) 102, storage 104, I/O system(s) 124, communication system(s) 126, and/or other components. In some implementations, the evidence extraction module is trained with a second set of ground truth to enable the evidence extraction module to identify references from one or more reference repositories that have content related to one or more particular types of claims. Furthermore, in some instances, act 1108 is performed in response to detecting the one or more claims within the textual content.

Act 1110 of flow diagram 1100 includes using the evidence extraction module to automatically search for one or more related references that have content that is determined by the evidence extraction module to be related to the detected one or more claims. Act 1110 is performed, in some instances, by a system 100 utilizing processor(s) 102, storage 104, evidence extraction module 112, I/O system(s) 124, communication system(s) 126, and/or other components. In some implementations, the evidence extraction module is configured to search one or more reference repositories for the one or more related references. In some instances, the one or more related references are identified by the evidence extraction module as related to the detected one or more claims based on the one or more related references satisfying a threshold of relevance to content of detected claims. Act 1110 may be performed in response to detecting the one or more claims within the textual content.

Act 1112 of flow diagram 1100 includes automatically determining whether the content in the one or more related references supports or refutes the one or more claims using a claim verification module. Act 1112 is performed, in some instances, by a system 100 utilizing processor(s) 102, storage 104, claim verification module 114, I/O system(s) 124, communication system(s) 126, and/or other components. In some implementations, the claim verification module is trained with a third set of ground truth to link detected claims to one or more pieces of evidence within related references and to determine whether the one or more pieces of evidence support or refute the one or more claims. In some instances, act 1112 is performed in response to identifying the one or more related references.

Act 1114 of flow diagram 1100 includes, in response to determining a set of references of the one or more related references supports or refutes the one or more claims, presenting at least one of (i) a support indicator or (ii) a refute indicator within the user interface in association with the one or more claims. Act 1114 is performed, in some instances, by a system 100 utilizing processor(s) 102, storage 104, I/O system(s) 124, communication system(s) 126, and/or other components. In some implementations, the set of references omits a particular reference that fails to satisfy a classification confidence threshold. The classification confidence threshold indicates a level of confidence in a determination by the claim verification module that a reference supports or refutes a claim.

In some implementations the support indicator visually indicates that the one or more claims are supported by evidence, and the refute indicator visually indicates that the one or more claims are refuted by evidence. In some instances, the support indicator or the refute indicator indicates a weight of support or weight of refutation for the one or more claims.

Furthermore, in some implementations, act 1114 entails additional actions, such as, in response to determining the set of references of the one or more related references supports the one or more claims, presenting the support indicator within the user interface in association with the one or more claims. In some instances, act 1114 entails, in response to determining the set of references of the one or more related references refutes the one or more claims, presenting the refute indicator within the user interface in association with the one or more claims. Act 1114 may additionally or alternatively entail presenting a representation of the set of references in the user interface in association with the one or more claims, presenting a representation of one or more pieces of evidence of the set of references in the user interface in association with the one or more claims, and/or presenting a recommendation for modifying the one or more claims based on the set of references.

Act 1116 of flow diagram 1100 includes receiving user input for refining the claim detection module, the evidence extraction module, and/or the claim verification module. Act 1116 is performed, in some instances, by a system 100 utilizing processor(s) 102, storage 104, claim detection module 110, evidence extraction module 112, claim verification module 114, I/O system(s) 124, communication system(s) 126, and/or other components. For example, in some implementations, act 1116 includes receiving user input indicating that a reference or a piece of evidence of the set of references is not relevant to the one or more claims and refining the evidence extraction module based on the user input indicating that the reference or the piece of evidence of the set of references is not relevant to the one or more claims. In some instances, act 1116 includes receiving user input indicating that a reference or a piece of evidence of the set of references fails to support the one or more claims and refining the claim verification module based on the user input indicating that the reference or the piece of evidence of the set of references fails to support the one or more claims.

Furthermore, in some implementations, act 1116 includes receiving user input indicating that a reference or a piece of evidence of the set of references fails to refute the one or more claims and refining the claim verification module based on the user input indicating that the reference or the piece of evidence of the set of references fails to refute the one or more claims. Additionally, or alternatively, act 1116 may include emphasizing one or more portions of the textual content determined by the claim detection module to be contextually associated with the one or more claims, receiving user input modifying the one or more portions of the textual content that are contextually associated with the one or more claims, and refining the claim detection module based on the user input modifying the one or more portions of the textual content that are contextually associated with the one or more claims.

Attention is now directed to FIG. 12. Act 1202 of flow diagram 1200 includes identifying a document comprising a body of text. Act 1202 is performed, in some instances, by a system 100 utilizing processor(s) 102, storage 104, I/O system(s) 124, communication system(s) 126, and/or other components. The document and the body of text may take on various forms as described hereinabove.

Act 1204 of flow diagram 1200 includes detecting one or more claims within the body of text using a claim detection module. Act 1204 is performed, in some instances, by a system 100 utilizing processor(s) 102, storage 104, claim detection module 110, I/O system(s) 124, communication system(s) 126, and/or other components. In some implementations, the claim detection module is trained to detect claims within bodies of text.

Act 1206 of flow diagram 1200 includes automatically searching within a corpus of references for one or more related references using an evidence extraction module. Act 1206 is performed, in some instances, by a system 100 utilizing processor(s) 102, storage 104, evidence extraction module 112, I/O system(s) 124, communication system(s) 126, and/or other components. In some implementations, the evidence extraction module is trained to identify related references from the corpus of references based on content of detected claims. Accordingly, the one or more related references are determined by the evidence extraction module to be relevant to the one or more claims. Furthermore, in some instances, act 1206 is performed in response to detecting the one or more claims within the body of text.

Act 1208 of flow diagram 1200 includes automatically determining whether the one or more related references support or refute the one or more claims using a claim verification module. Act 1208 is performed, in some instances, by a system 100 utilizing processor(s) 102, storage 104, claim verification module 114, I/O system(s) 124, communication system(s) 126, and/or other components. In some implementations, the claim verification module is trained to link detected claims to one or more pieces of evidence within related references from the corpus of references and determine whether the one or more pieces of evidence support or refute the one or more claims. Furthermore, in some instances, act 1208 is performed in response to identifying the one or more related references.

Act 1210 of flow diagram 1200 includes in response to determining a set of supporting references of the one or more related references that supports the one or more claims, generating a modified document that includes a support indicator in association with the one or more claims, or, in response to determining a set of refuting references of the one or more related references that refutes the one or more claims, generating a modified document that includes a refute indicator in association with the one or more claims. Act 1210 is performed, in some instances, by a system 100 utilizing processor(s) 102, storage 104, I/O system(s) 124, communication system(s) 126, and/or other components. In some instances, the support indicator indicates that the one or more claims are supported by evidence, and the refute indicator indicates that the one or more claims are refuted by evidence.

Act 1212 of flow diagram 1200 includes determining that the corpus of references has been updated. Act 1212 is performed, in some instances, by a system 100 utilizing processor(s) 102, storage 104, I/O system(s) 124, communication system(s) 126, and/or other components. A corpus of references may be updated in various ways as described hereinabove. Furthermore, an update to the corpus of references may be detected in various ways as described hereinabove.

Act 1214 of flow diagram 1200 includes redetermining whether the one or more related references support or refute the one or more claims using the claim verification module. Act 1214 is performed, in some instances, by a system 100 utilizing processor(s) 102, storage 104, evidence extraction module 112, claim verification module 114, I/O system(s) 124, communication system(s) 126, and/or other components. In some instances, act 1214 is performed in response to determining that the corpus of references has been updated.

Act 1216 of flow diagram 1200 includes generating an updated modified document that includes one or more updates to the support indicator or the refute indicator. Act 1216 is performed, in some instances, by a system 100 utilizing processor(s) 102, storage 104, I/O system(s) 124, communication system(s) 126, and/or other components. The modified document may be generated by modifying an existing document or generating a new document.

Act 1218 of flow diagram 1200 includes generating a notification for an entity associated with the updated modified document. Act 1202 is performed, in some instances, by a system 100 utilizing processor(s) 102, storage 104, I/O system(s) 124, communication system(s) 126, and/or other components. The notification may take on various forms and may be delivered in various ways as discussed hereinabove. Furthermore, act 1218 may be performed in response to the updated modified document including the one or more updates to the support indicator or the refute indicator.

Attention is now directed to FIG. 13. Act 1302 of flow diagram 1300 includes receiving a document comprising a body of text. Act 1302 is performed, in some instances, by a system 100 utilizing processor(s) 102, storage 104, I/O system(s) 124, communication system(s) 126, and/or other components. The document and the body of text may take on various forms as described hereinabove.

Act 1304 of flow diagram 1300 includes detecting a plurality of claims within the body of text using a claim detection module. Act 1302 is performed, in some instances, by a system 100 utilizing processor(s) 102, storage 104, claim detection module 110, I/O system(s) 124, communication system(s) 126, and/or other components. In some instances, the claim detection module is trained to detect claims within bodies of text.

Act 1306 of flow diagram 1300 includes automatically searching within a corpus of references for a plurality of sets of related references using an evidence extraction module. Act 1306 is performed, in some instances, by a system 100 utilizing processor(s) 102, storage 104, evidence extraction module 112, I/O system(s) 124, communication system(s) 126, and/or other components. In some implementations, the evidence extraction module is trained to identify related references from the corpus of references based on content of detected claims. Furthermore, in some instances, each set of related references of the plurality of sets of references is determined by the evidence extraction module to be relevant to a respective claim of the plurality of claims.

Act 1308 of flow diagram 1300 includes for each respective claim of the plurality of claims, automatically determining whether a respective set of related references of the plurality of sets of references supports or refutes the respective claim using a claim verification module. Act 1308 is performed, in some instances, by a system 100 utilizing processor(s) 102, storage 104, claim verification module 114, I/O system(s) 124, communication system(s) 126, and/or other components. In some implementations, the claim verification module is trained to link detected claims to one or more pieces of evidence within related references from the corpus of references and to determine whether the one or more pieces of evidence support or refute the one or more claims.

Act 1310 of flow diagram 1300 includes based on the determination of whether each respective set of related references supports or refutes each respective claim, generating a veracity score for the document. Act 1310 is performed, in some instances, by a system 100 utilizing processor(s) 102, storage 104, claim verification module 114, I/O system(s) 124, communication system(s) 126, and/or other components. In some instances, the veracity score indicates a level of evidentiary support for claims present in the document. Act 1310 may entail additional acts, such as presenting a representation of the veracity score for display on a user interface and/or associating the veracity score with the content creator.

Act 1312 of flow diagram 1300 includes determining that the corpus of references has been updated. Act 1312 is performed, in some instances, by a system 100 utilizing processor(s) 102, storage 104, I/O system(s) 124, communication system(s) 126, and/or other components. A corpus of references may be updated in various ways as described hereinabove. Furthermore, an update to the corpus of references may be detected in various ways as described hereinabove.

Act 1314 of flow diagram 1300 includes generating an updated veracity score for the document. Act 1314 is performed, in some instances, by a system 100 utilizing processor(s) 102, storage 104, claim verification module 114, I/O system(s) 124, communication system(s) 126, and/or other components. In some instances, act 1314 is performed in response to determining that the corpus of references has been updated.

Example Techniques for Facilitating Procedure Optimization

Figure 14A:
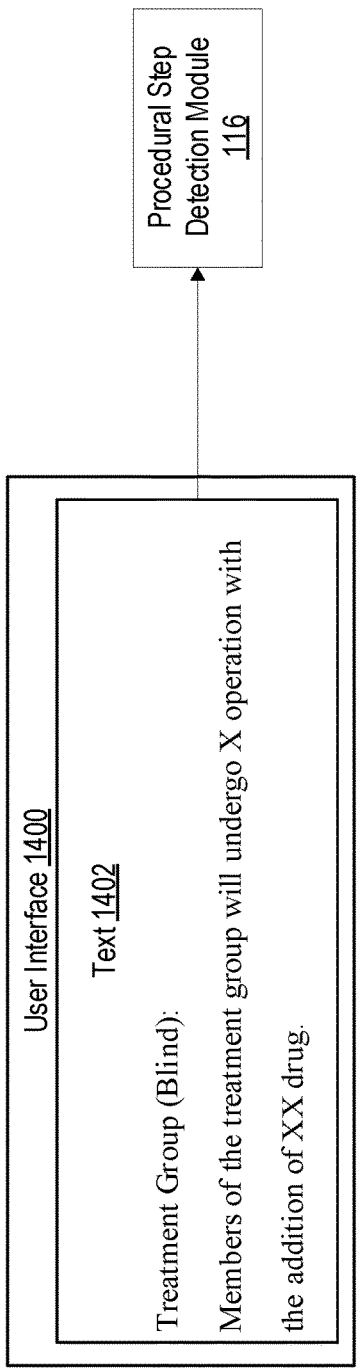
FIGS. 14A and 14B illustrates an example of detecting procedural steps within a body of text using a procedural step detection module.

Attention is now directed to FIG. 14A, which illustrates an example of detecting procedural steps within a body of text 1402 using a procedural step detection module 116. In particular, FIG. 14A shows a selection of a body of text (i.e., text 1402) represented within a user interface 1400, which may be at least partially similar to the user interface 200 discussed hereinabove with reference to FIGS. 2A and 2B. Although the present example focuses, in at least some respects, on text 1402 represented within a user interface 1400, one will appreciate, in view of the present disclosure, that the techniques described herein may be used to detect procedural steps within textual content regardless of whether the textual content is represented in a user interface.

FIG. 14A shows that the text 1402 represented within the user interface 1400 includes a particular selection of text that states, "Treatment Group (Blind): Members of the treatment group will undergo X operation with the addition of XX drug." This example selection of text includes a procedural step whereby members of a treatment group will receive a particular operation (i.e., X operation) with the addition of a particular drug (XX drug). As described herein, systems and methods of the present disclosure are configurable to analyze detected procedural steps to determine whether such procedural steps are associated with detrimental results in view of information available in a corpus or repository of references. The subject matter and content of the text 1402 is provided for the sake of explanation only and is not limiting of the types of textual content on which the techniques of the present disclosure may be utilized.

In some instances, the text 1402 is generated by a user within a text authoring context or is navigated to or selected by a user within a text navigation/viewing context. For example, a user creating a standard operating procedure (SOP) document or clinical trial protocol document may access an existing SOP or clinical trial protocol document using document authoring software and use the existing SOP or clinical trial protocol as a starting point for creating a new or modified SOP or clinical trial protocol. In some instances, analysis of procedural steps represented within a body of text is triggered in response to user input (e.g., user input selecting one or more portions of text for analysis), whereas in some instances, analysis of procedural steps is performed automatically (e.g., in real-time during document authoring or navigation).

Regardless of how the text 1402 is obtained or identified by a system (e.g., system 100), a system may access a procedural step detection module 116 to facilitate the automatic identification of procedural steps represented within the body of text. In some implementations, the procedural step detection module 116 is trained using a set of ground truth data to enable the procedural step detection module 116 to detect occurrences of procedural steps within text (e.g., text 1402), which may be regarded as a sentence labeling task. For example, in some instances, the procedural step detection module 116 comprises or is based on a natural language processing (NLP) model that is configured to analyze the parts of speech and/or other content of a body of text to detect particular language and/or context associated with procedural steps or acts.

In some implementations, the procedural step detection module 116 is initially or further trained using tagged training data under a full supervision or weak supervision training approach. For instance, the tagged training data may include domain-specific or enterprise-specific textual content that includes tags that indicate procedural steps represented in the textual content (e.g., tags applied to procedure documents or portions of documents of an organization).

Aside from explicit tags, other artifacts or data may be used to train a procedural step detection module 116. For example, many documents, papers, records, and publications include headings indicating whether the text that follows the heading corresponds to a method, procedure, process, or protocol. Thus, textual content following a heading or label associated with a procedure, method, process, protocol, or related term may additionally or alternatively be used as training data for training a procedural step detection module 116.

Accordingly, a procedural step detection module 116 may be trained or configured to analyze the content and context of input text in a deep manner, enabling the recognition of procedural steps within the input text. One will appreciate, in view of the present disclosure, that a procedural step detection module 116 may operate in a cross-domain or multi-domain manner or be tailored to specific technical fields, industries, enterprises, or even types of procedural steps. In some instances, the operation of a procedural step detection module 116 is selectively modifiable by a user. For example, a user may provide user input specifying one or more types of procedural steps the procedural step detection module 116 will detect within a body of text (e.g., procedural steps related to particular subject matter). Multiple procedural step detection modules 116 may exist within a single system for use in different contexts.

Figure 14B:

FIG. 14A conceptually represents inputting the text 1402 into the procedural step detection module 116 to detect one or more procedural steps within the text 1402. FIG. 14B illustrates an example of a procedural step 1404 detected by the procedural step detection module 116 in response to receiving the text 1402 as input. The procedural step 1404 is represented in FIG. 14B as an underlined portion of the text 1402. In the example shown in FIG. 14B.

Although FIG. 14B omits underlining or other emphasis of portions of the text 1402 that are contextually related to the procedural step 1404, such portions may be emphasized for viewing by a user in accordance with the present disclosure (e.g., similar to the discussion of FIG. 2B above). Furthermore, it should be noted that a user may provide user input for modifying the procedural steps identified by the procedural step detection module 116 to facilitate further training or refining of the procedural step detection module 116 to improve the accuracy of the procedural step detection module 116 in detecting procedural steps (e.g., similar to the discussion of FIG. 2B above).

Figure 15:
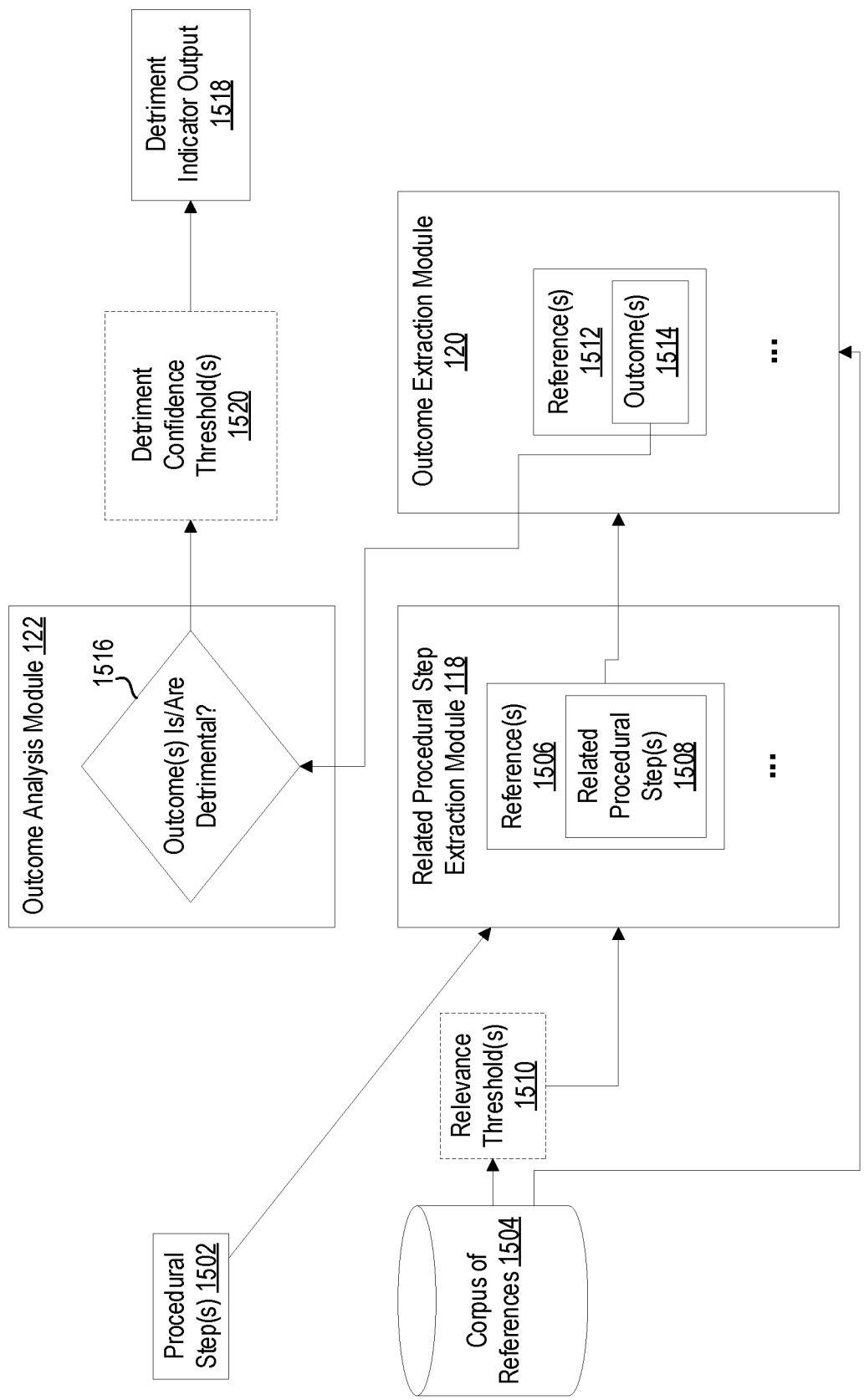
FIG. 15 illustrates a conceptual representation of extracting related procedural steps from a corpus of references using a related procedural step extraction module, extracting outcomes associated with the related procedural steps using an outcome extraction module, and analyzing the outcomes using an outcome analysis module.

FIG. 15 illustrates a conceptual representation of extracting related procedural steps from a corpus of references 1504 using a related procedural step extraction module 118, extracting outcomes associated with the related procedural steps using an outcome extraction module 120, and analyzing the outcomes using an outcome analysis module 122. In particular, FIG. 15 illustrates procedural step(s) 1502, which may correspond to the procedural step 1404 according to the example shown and described with reference to FIGS. 14A and 14B, or any other procedural step(s) detected using a procedural step detection module 116. FIG. 15 also shows that the procedural step(s) 1502 may be provided as input to a related procedural step extraction module 118. In some instances, a system accesses the related procedural step extraction module 118 and provides procedural step(s) 1502 as input thereto automatically in response to detecting the procedural step(s) 1502 within a body of text.

The corpus of references 1504 may comprise any set or collection of documents, papers, publications, and/or other works that comprise information available for determining whether procedural step(s) 1502 are associated with detrimental outcomes. In some instances, a corpus of references 1504 includes is tailored to one or more particular domains (e.g., biological sciences, security operations centers, pharmaceuticals, etc.) and/or particular entities (e.g., comprising documents or artifacts generated by one or more commercial, public, or other entities). In other instances, the corpus of references 1504 includes index of content accessible via the internet. A corpus of references 1504 may be stored and accessible in any form or format, without limitation.

In some implementations, the related procedural step extraction module 118 is trained using a set of ground truth data to enable the related procedural step extraction module 118 to identify references from the corpus of references 1504 that include procedural steps that are related to procedural steps detected via a procedural step detection module 116 (e.g., procedural step(s) 1502). The set of ground truth data used to train the related procedural step extraction module 118 may be different from or at least partially overlap with the set of ground truth data used to train the procedural step detection module 116. In some instances, the related procedural step extraction module 118 is implemented as a recall model or retrieval model configured to search through the corpus of references 1504 in a lightweight and rapid manner for procedural steps that are similar to one or more detected procedural steps (e.g., procedural step(s) 1502). For example, the related procedural step extraction module 118 may operate in a term-based or token-based manner, such as by determining overlap between terms or entities associated with a detected procedural step and terms or entities associated with one or more references of the corpus of references 1504 (e.g., via determining a vector dot product). In some instances, the related procedural step extraction module 118 utilizes embedding-based retrieval (e.g., by analyzing semantic relevance between words) or a combination of embedding-based and term-based retrieval.

In some implementations, the related procedural step extraction module 118 is initially or further trained using tagged training data under a full supervision or weak supervision training approach. For instance, the tagged training data may include domain-specific or enterprise-specific textual content that includes tags that link related procedural steps to related procedural steps. For example, a pharmaceutical company may track provenance between different clinical trial protocols, indicating which procedural steps are derived from past clinical trial protocols. This provenance tracking may be used as an indication that different procedural steps are related for training a related procedural step extraction module 118. Aside from the clinical trial protocol context, similar training input identifying related procedural steps may be obtained for other domains or enterprises using other domain-specific or enterprise-specific data.

Furthermore, many artifacts that are not necessarily domain-specific or enterprise-specific may be used to form a weak supervision signal for training a related procedural step extraction module 118. For example, many research papers, legal documents, and/or other types of formal publications include citations associated with procedural steps present within the paper, document, or publication. For example, citations from one procedural document referring to another procedural document may provide an indication that procedural steps within one document are related to procedural steps within the other document. Thus, in some instances, citations between procedural documents may be used as training input for training a related procedural step extraction module 118 in an at least partially supervised manner.

Accordingly, in some implementations, a related procedural step extraction module 118 is trained or configured to identify reference(s) 1506 and/or related procedural step(s) 1508 within reference(s) 1506 that are related to one or more detected procedural steps (e.g., procedural step(s) 1502). One will appreciate, in view of the present disclosure, that a related procedural step extraction module 118 may operate in a cross-domain or multi-domain manner or be tailored to specific technical fields, industries, enterprises, or even types of procedural steps.

In some instances, a related procedural step extraction module 118 identifies reference(s) 1506 or related procedural step(s) 1508 from reference(s) 1506 as being related to a detected procedural step (e.g., procedural step(s) 1502) by calculating a relevance score for the reference or potentially related procedural step and determining that the calculated relevance score satisfies relevance threshold(s) 1510 (e.g., a threshold relevance score). A relevance score may take on various forms, such as a vector dot product value or any numerical value configured to represent semantic overlap between terms of a procedural step and terms of a reference or potentially related procedural step within a reference. The related procedural step extraction module 118 may refrain from obtaining or selecting references or potentially related procedural steps from a corpus of references 1504 that fail to satisfy the relevance threshold(s) 1510.

Relevance threshold(s) 1510 may comprise a particular relevance score that a reference or procedural step within a reference must satisfy to be determined by the related procedural step extraction module 118 to be related to a particular detected procedural step (e.g., detected via the procedural step detection module 116). In some instances, relevance threshold(s) 1510 used by the related procedural step extraction module 118 is/are selectively modifiable by a user (e.g., via user input), allowing users to modify the breadth or focus of the reference(s) 1506 and/or related procedural step(s) 1508 identified by the related procedural step extraction module 118 as being related to the detected procedural step (e.g., procedural step(s) 1502). The ellipsis within the related procedural step extraction module 118 as represented in FIG. 15 indicates that a related procedural step extraction module 118 may determine that any number of references(s) 1506 or related procedural step(s) 1508 is/are relevant to procedural step(s) 1502.

In some instances, the operation of a related procedural step extraction module 118 is selectively modifiable by a user. For example, a user may provide user input specifying one or more types of references or related procedural steps the related procedural step extraction module 118 will search for within the corpus of references 1504 (e.g., references that the user finds reputable or desirable). For instance, a user may specify particular fields of study, standards, bodies, publications, journals, etc. for the related procedural step extraction module 118 to search for within the corpus of references 1504.

As another example, a user may specify a number of references and/or related procedural steps that the related procedural step extraction module 118 will obtain from the corpus of references 1504 for further analysis. Multiple related procedural step extraction modules 118 may exist within a single system for use in different contexts.

FIG. 15 illustrates the outcome extraction module 120, which is configured to identify outcomes associated with the related procedural step(s) 1508 (or outcomes associated with the procedural step(s) 1502). The outcomes may be identified from the reference(s) 1506 that comprise the related procedural step(s) 1508 and/or from other information of the corpus of references 1504 (as indicated in FIG. 15 by the lines extending from the reference(s) 1506 and from the corpus of references 1504 toward the outcome extraction module 120.

In some implementations, the outcome extraction module 120 is trained using a set of ground truth data to enable the outcome extraction module 120 to identify outcomes from the reference(s) 1506 and/or the corpus of references 1504 that are associated with the related procedural step(s) 1508 (e.g., identified by the related procedural step extraction module 118). The set of ground truth data used to train the outcome extraction module 120 may be different from or at least partially overlap with the set of ground truth data used to train the procedural step detection module 116 and/or the set of ground truth data used to train the related procedural step extraction module 118.

In some instances, the outcome extraction module 120 is implemented as a recall model or retrieval model configured to search through the reference(s) 1506 for outcomes that follow or result from the related procedural step(s) 1508. In some instances, the outcome extraction module 120 comprises or is based on an NLP model that is configured to analyze the parts of speech and/or other content of a body of text to detect particular language and/or context associated with outcomes or results.

Furthermore, to determine whether a detected outcome is associated with a related procedural step, the outcome extraction module 120 may operate in a term-based or token-based manner, such as by determining overlap between terms or entities associated with a related procedural step 1508 and other terms or entities associated with the reference(s) 1506 and/or other portions of the corpus of references 1504 (e.g., via determining a vector dot product). In some instances, the outcome extraction module 120 utilizes embedding-based retrieval (e.g., by analyzing semantic relevance between words) or a combination of embedding-based and term-based retrieval. In some instances, the outcome extraction module 120 comprises a language model that allows the outcome extraction module 120 to determine whether an outcome is associated with a procedural step based on proximity or contextual relation (e.g., detecting that the outcome and the related procedural step are within the same sentence or paragraph or detecting contextual or explicit referencing between the outcome and the related procedural step).

In some implementations, the outcome extraction module 120 is initially or further trained using tagged training data under a full supervision or weak supervision training approach. Furthermore, aside from explicitly tagged data, other types of data may be used to provide a training signal for training the outcome extraction module 120. For example, many documents that include the results of a procedure (e.g., research papers, outcome reporting forms, etc.) include explicit labeling associated with the results (e.g., labeling of a "results", "findings", "outcomes" or similar section). Thus, in some instances, labels, headings, or other structures within documents may be used to link outcomes to procedural steps and may thereby be used as a weak supervision signal for training an outcome extraction module 120.

Still furthermore, in some instances, outcome reports may explicitly cite to other documents that include the procedures related to the outcomes. Such citations may therefore be used to link outcomes to procedural steps and may thereby be used as a weak supervision signal for training an outcome extraction module 120.

Accordingly, in some implementations, an outcome extraction module 120 is trained or configured to identify outcome(s) 1514 that are related to related procedural step(s) 1508. The outcome(s) 1514 may be part of reference(s) 1512, which may include reference(s) 1506 and/or different or additional references from the corpus of references 1504. One will appreciate, in view of the present disclosure, that an outcome extraction module 120 may operate in a cross-domain or multi-domain manner or be tailored to specific technical fields, industries, enterprises, or even types of procedural steps. The ellipsis within the outcome extraction module 120 as represented in FIG. 15 indicates that an outcome extraction module 120 may determine that any number of outcome(s) 1514 is/are associated with the related procedural step(s) 1508.

In some instances, the operation of an outcome extraction module 120 is selectively modifiable by a user. For example, a user may provide user input specifying one or more types of outcomes the outcome extraction module 120 will search for within the corpus of references 1504. Furthermore, in some instances, a user may specify particular types of references for the outcome extraction module 120 to search through for outcomes within the corpus of references 1504.

As another example, a user may specify a number of outcomes that the outcome extraction module 120 will obtain for further analysis. Multiple outcome extraction modules 120 may exist within a single system for use in different contexts. As noted above, the functions of the related procedural step extraction module 118 and the outcome extraction module 120 may be combined for performance by any number of modules (e.g., one or more modules).

FIG. 15 conceptually represents the outcome analysis module 122 in association with a decision block 1516 and shows a line extending from the outcome(s) 1514 toward the decision block 1516. The decision block 1516 includes determining whether "outcome(s) is/are detrimental", indicating that, in some implementations, the outcome analysis module 122 is trained to determine whether an outcome (e.g., outcome(s) 1514 obtained via the outcome extraction module 120) comprises a detrimental outcome.

In some implementations, the outcome analysis module 122 is trained using a set of ground truth data to enable the outcome analysis module 122 to determine whether an outcome is detrimental. The set of ground truth data used to train the outcome analysis module 122 may be different from or at least partially overlap with the set of ground truth data used to train the procedural step detection module 116, the set of ground truth data used to train the related procedural step extraction module 118, and/or the set of ground truth data used to train the outcome extraction module 120.

In some instances, the outcome analysis module 122 comprises or is based on an NLP model that is configured to analyze the parts of speech and/or other content of a body of text (e.g., the use of language associated with detriment, failure, unsuccessfulness, frustration of purpose, etc.) to detect particular language and/or context associated with negative results or detrimental outcomes. In some implementations, the outcome analysis module 122 is initially or further trained using tagged training data under a full supervision or weak supervision training approach. For instance, the tagged training data may include domain-specific or enterprise-specific textual content that includes tags that indicate that a result or outcome is detrimental. Furthermore, many entities maintain logs or records of the outcomes of procedures that include explicit indications of whether the procedure or result was successful (e.g., a binary classification of success or failure). Such data may therefore be used to additionally or alternative train an outcome analysis module 122.

Accordingly, in some implementations, an outcome analysis module 122 is trained or configured to determine whether an outcome is detrimental based on a deep contextual understanding of the extracted outcome(s) 1514. One will appreciate, in view of the present disclosure, that an outcome analysis module 122 may operate in a cross-domain or multi-domain manner or be tailored to specific technical fields, industries, enterprises, or even types of outcomes.

In this regard, an outcome analysis module 122 is configurable to determine a set of outcomes that are or include detrimental results. FIG. 15 furthermore illustrates that, in some implementations, a system is configured to generate detriment indicator output 1518 based on a determination of a set of outcomes that include detrimental results. The detriment indicator output 1518 visually indicates (e.g., on a user interface) that the procedural step(s) 1502 are associated with detrimental results (e.g., based on being related to the related procedural step(s) 1508 that are associated with outcome(s) 1514 that are determined to be detrimental by the outcome analysis module 122). Additional details concerning detriment indicators will be provided hereinafter.

In some implementations, the outcome analysis module 122 associates a detriment confidence score with its determination that an outcome is detrimental. The detriment confidence score may numerically represent an amount of confidence in the detriment label assigned to an outcome (e.g., based on an error or loss metric).

Furthermore, in some implementations, a system is configured to omit one or more outcomes from the set(s) of outcomes determined by the outcome analysis module 122 to be detrimental where the one or more outcomes fail to satisfy detriment confidence threshold(s) 1520. The detriment confidence threshold(s) 1520 may comprise a particular detriment confidence score (e.g., 50% or greater) that an outcome must satisfy to be determined by the outcome analysis module 122 to be detrimental. In some instances, the detriment confidence threshold(s) 1520 is/are modifiable by a user (e.g., via user input), allowing users to modify the breadth or focus of the outcomes determined by the outcome analysis module 122 to be detrimental.

In this way, systems of the present disclosure are configurable to determine whether procedural steps are associated with detrimental results by detecting procedural steps within a body of text using a procedural step detection module 116, identifying related procedural steps and associated outcomes using, respectively, a related procedural step extraction module 118 and an outcome extraction module 120, and determining whether the outcomes are detrimental using an outcome analysis module 122. Such functionality may allow users to create procedures in a manner that maximizes the benefit from previously performed procedures by allowing users to omit or modify procedures determined to be associated with detrimental results (relative to a corpus of references).

One will appreciate, in view of the present disclosure, that analysis of whether procedural step(s) 1502 is/are associated with detrimental results may be performed in response to detecting updates to the corpus of references 1504. Such updates to a corpus of references may trigger the generation of a modified document or updated modified document including an initially analyzed procedure (e.g., similar to the discussion hereinabove of FIG. 9). For example, a procedural act that was initially thought to be associated with detrimental results may no longer be regarded as associated with detrimental results in view of an update to a corpus of references. A notification may be generated for an entity associated with the document and/or procedural step.

Figure 16:
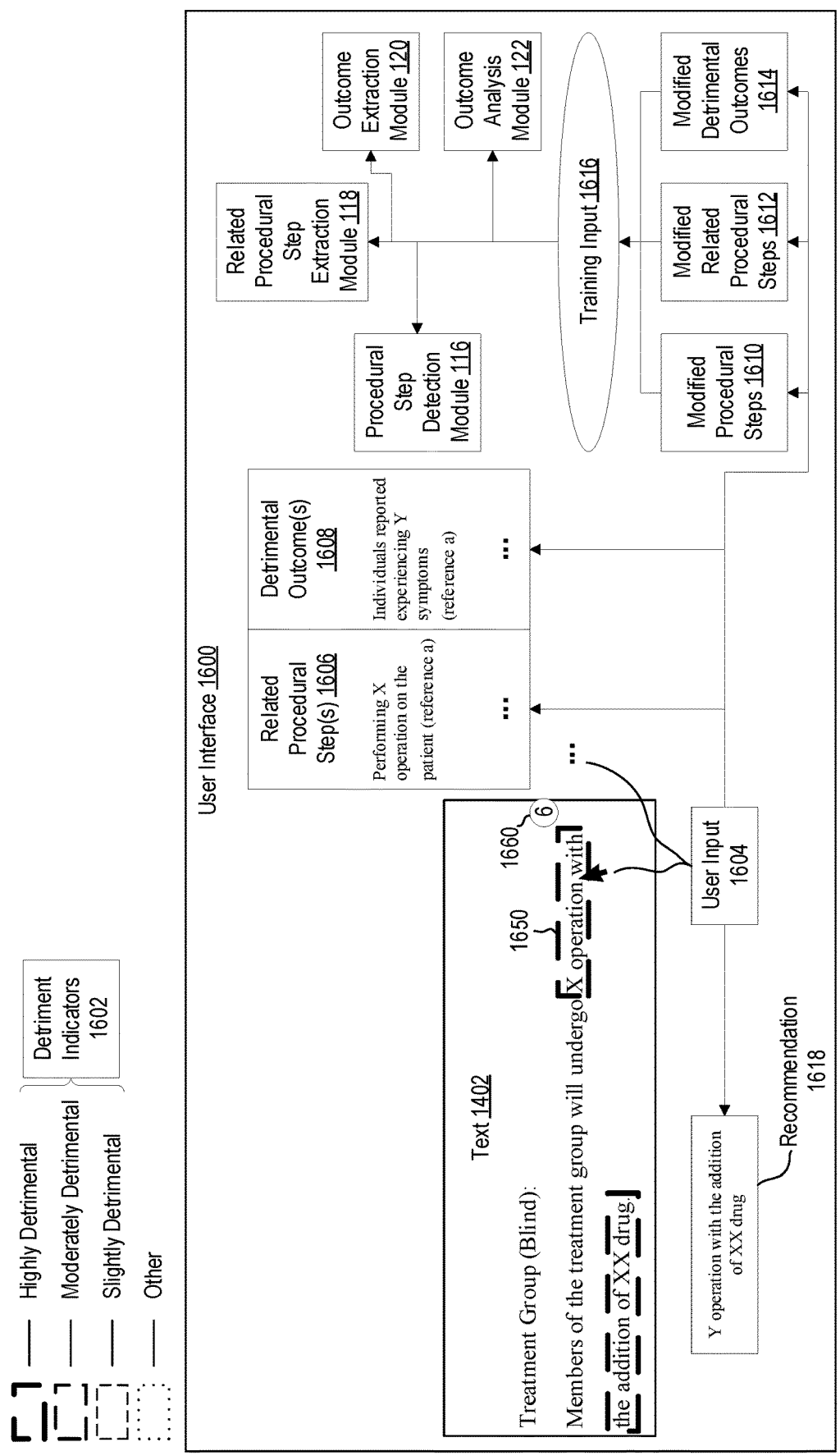
FIG. 16 illustrates examples of detecting user input directed at a detriment indicator and examples of actions that may be performed and/or content that may be displayed in response to the user input.

FIG. 16 illustrates examples of detecting user input 1604 directed at a detriment indicator or other elements and illustrates examples of actions that may be performed and/or content that may be displayed in response to the user input 1604. FIG. 16 illustrates that the detriment indicator output 1518 discussed above with reference to FIG. 15 may comprise or cause presentation of one or more detriment indicators 1602 within a user interface 1600 and in association with one or more procedural steps represented in the text 1402 (e.g., procedural steps identified or detected for analysis for association with detrimental results, as described above).

FIG. 16 depicts the detriment indicators 1602 as dashed rectangles. FIG. 16 also illustrates that detriment indicators 1602 may take on various forms to indicate a weight of detriment for the analyzed procedural step. For instance, FIG. 16 shows an example in which the detriment indicators 1602 include a first type with a thick linewidth indicating that a procedural step is highly associated with detrimental results (or is associated with results that are highly detrimental), a second type with a moderate linewidth indicating that a procedural step is moderately associated with detrimental results (or is associated with results that are moderately detrimental), and a third type with a thin linewidth indicating that a procedural step is slightly associated with detrimental results (or is associated with results that are slightly detrimental). The weight of detriment may be determined based on various factors and may differ for different domains. For example, in some implementations, a weight of detriment is determined based on the number of recorded detrimental outcomes associated with the procedural step, or the severity of the outcomes identified (e.g., symptom severity, number of persons affected, cost of replacement or repair, loss of profit, etc.)

The example depicted in FIG. 16 shows that the procedural step of performing X operation with the addition of XX drug is associated with a detriment indicator 1650, indicating that the procedural step of performing X operation with the addition of XX drug is highly detrimental (e.g., as determined using the related procedural step extraction module 118, the outcome extraction module 120, and the outcome analysis module 122).

In this way, a user interacting with the user interface may become informed as to whether procedural steps represented within the text 1402 is/are associated with detrimental results, whether or not the user generated the text 1402 and potentially in real-time.

FIG. 16 also illustrates an example additional indicator represented as a dotted rectangle and classified as "other", which may have different uses in different implementations. For example, in some implementations, the additional indicator indicates that a procedural step is associated with both detrimental results and positive results (relative to a corpus of references).

The example shown in FIG. 16 is illustrative only and non-limiting, and detriment indicators 1602 may be embodied in other ways (e.g., using different colors or shades to depict weight of detriment). Furthermore, in some instances, the detriment indicators 1602 do not indicate a weight of detriment for associated procedural steps.

As noted above, FIG. 16 illustrates user input 1604 directed to the detriment indicator 1650 associated with the procedural step of performing X operation with the addition of XX drug, as represented within the text 1402 of the user interface 1600. As indicated above, the user input 1604 may take on various forms (e.g., hover input, selection input via clicking or tapping, voice or gesture input, etc.). FIG. 16 shows an example in which a system, in response to the user input 1604 directed to the detriment indicator 1650 associated with the procedural step is configured to display a number of references or outcomes 1660 that indicate that the procedural step is associated with detrimental results. The number of references or outcomes 1660 may comprise an additional or alternative indication of the weight of detriment for the procedural step.

FIG. 16 illustrates a representation of related procedural step(s) 1606 and detrimental outcome(s) 1608 being displayed within the user interface 1600 in association with the detriment indicator 1650 (or in association with the procedural step or displayed number of references or outcomes 1660 associated with the detriment indicator 1650). The related procedural step(s) 1606 may comprise one or more related procedural steps of a set of related procedural steps determined by the related procedural step extraction module 118 to be related to the procedural step of performing X operation with the addition of XX drug. As shown in FIG. 16, the related procedural step(s) 1606 include "Performing X operation on the patient" and indicates that the related procedural step is found in reference a.

Furthermore, the detrimental outcome(s) 1608 may comprise one or more outcomes that are associated with the related procedural step(s) 1606 as determined by the outcome extraction module 120. As shown in FIG. 16, the detrimental outcome(s) 1608 include "Individuals reported experiencing Y symptoms" and indicates that the outcome is found in reference a (one will appreciate, in view of the present disclosure, that an outcome associated with a related procedural step may be found in the same reference or a different reference). In some instances, the related procedural step(s) 1606 and the detrimental outcome(s) 1608 are organized in a table or other logical structure to allow users to readily ascertain which detrimental outcome(s) are associated with which related procedural step(s) 1606.

The presentation of the related procedural step(s) 1606 and/or the detrimental outcome(s) 1608 may allow users to readily perceive and/or interact with the related procedural step(s) 1606 and/or the detrimental outcome(s) 1608 determined to be related to or associated with the procedural step(s) represented in the text 1402. For example, in some implementations, the related procedural step(s) 1606 and/or the detrimental outcome(s) 1608 may include link functionality, allowing users to quickly navigate to one or more of the references that underlie the related procedural step(s) 1606 and/or the detrimental outcome(s) 1608 for further analysis or review or other purposes.

As noted above, FIG. 16 illustrates an example of user input 1604 directed to various elements represented within the user interface 1600 of FIG. 16. For instance, FIG. 16 shows that the user input 1604 may be directed to a detriment indicator 1650 and/or a portion of the text 1402 associated with the detriment indicator 1650. The user input 1604 may additionally or alternatively be directed to other elements, such as the number of references or outcomes 1660, the related procedural step(s) 1606, the detrimental outcome(s) 1608, etc. (as indicated by the ellipsis).

User input may trigger a system to perform various operations and/or display various content. For example, the number of references or outcomes 1660, the related procedural step(s) 1606, and/or the detrimental outcome(s) 1608 may be displayed in response to user input directed to the detriment indicator 1650 (or another element). As another example, in some instances, a system is configured to provide a recommendation 1618 for modifying the procedure associated with the detriment indicator 1650 in response to user input (or automatically). As shown in FIG. 16, the recommendation 1618 includes modifying the text 1402 to state performing "Y operation with the addition of XX drug", suggesting that users refrain from performing X operation in view of the outcomes associated therewith (e.g., in view of the outcome(s) 1608 associated with the procedural step(s) 1606 that are related to the procedural step detected within the text 1402).

Additionally, or alternatively, the user input 1604 may cause modifications to various elements within the user interface 1600 and may thereby trigger additional training or refinement for one or more of the procedural step detection module 116, the related procedural step extraction module 118, the outcome extraction module 120, or the outcome analysis module 122. For example, in some instances, the system is configured to emphasize or highlight one or more portions of the text 1402 that are contextually associated with the procedural step(s) detected by the procedural step detection module 116. Emphasis may comprise displaying the detriment indicator 1650 or another indicator in association with text that forms the detected procedural step. The user input 1604 may indicate that the procedural step is being misidentified by the procedural step detection module 116 and may further modify the text or presentation of the detected procedural step (or the detriment indicator 1650) to form modified procedural steps 1610. The modified procedural steps 1610 (and/or the user input resulting in them) may be used as training input for refining the procedural step detection module 116.

As another example, the user input 1604 may be directed to one or more of the related procedural step(s) 1606 determined by the related procedural step extraction module 118 to be related to the procedural step detected from the text 1402 via the procedural step detection module 116. The user input 1604 may result in modified related procedural steps 1612. For example, a user may determine that a related procedural step determined to be related to the procedural step detected from the text 1402 is in fact not related to the detected procedural step. Thus, the user input 1604 may indicate the mischaracterization of the related procedural step by the related procedural step extraction module, resulting in the modified related procedural steps 1612, which may be used as training input 1616 to refine the related procedural step extraction module 118.

In yet another example, the user input 1604 may be directed to one or more of the detrimental outcome(s) 1608 determined to be associated with the related procedural step(s) 1606 by the outcome extraction module 120 and determined to be detrimental by the outcome analysis module 122. In some instances, the user input 1604 indicates that an outcome determined by the outcome extraction module 120 to be associated with a corresponding related procedural step (e.g., of the related procedural step(s) 1606) is in fact not associated with the corresponding related procedural step. Thus, the user input 1604 may indicate the incorrect association of the outcome with the corresponding procedural step by the outcome extraction module 120, resulting in modified detrimental outcomes 1614, which may be used as training input 1616 to refine the outcome extraction module 120. In some instances, the user input 1604 indicates that an outcome determined to be detrimental by the outcome analysis module 122 is in fact not associated with detrimental results. Thus, the user input 1604 may correct the mischaracterization of the outcome by the outcome analysis module 122, resulting in modified detrimental outcomes 1614, which may be used as training input 1616 to refine the outcome analysis module 122.

Example Method(s) for Facilitating Procedure Optimization

Figure 17:
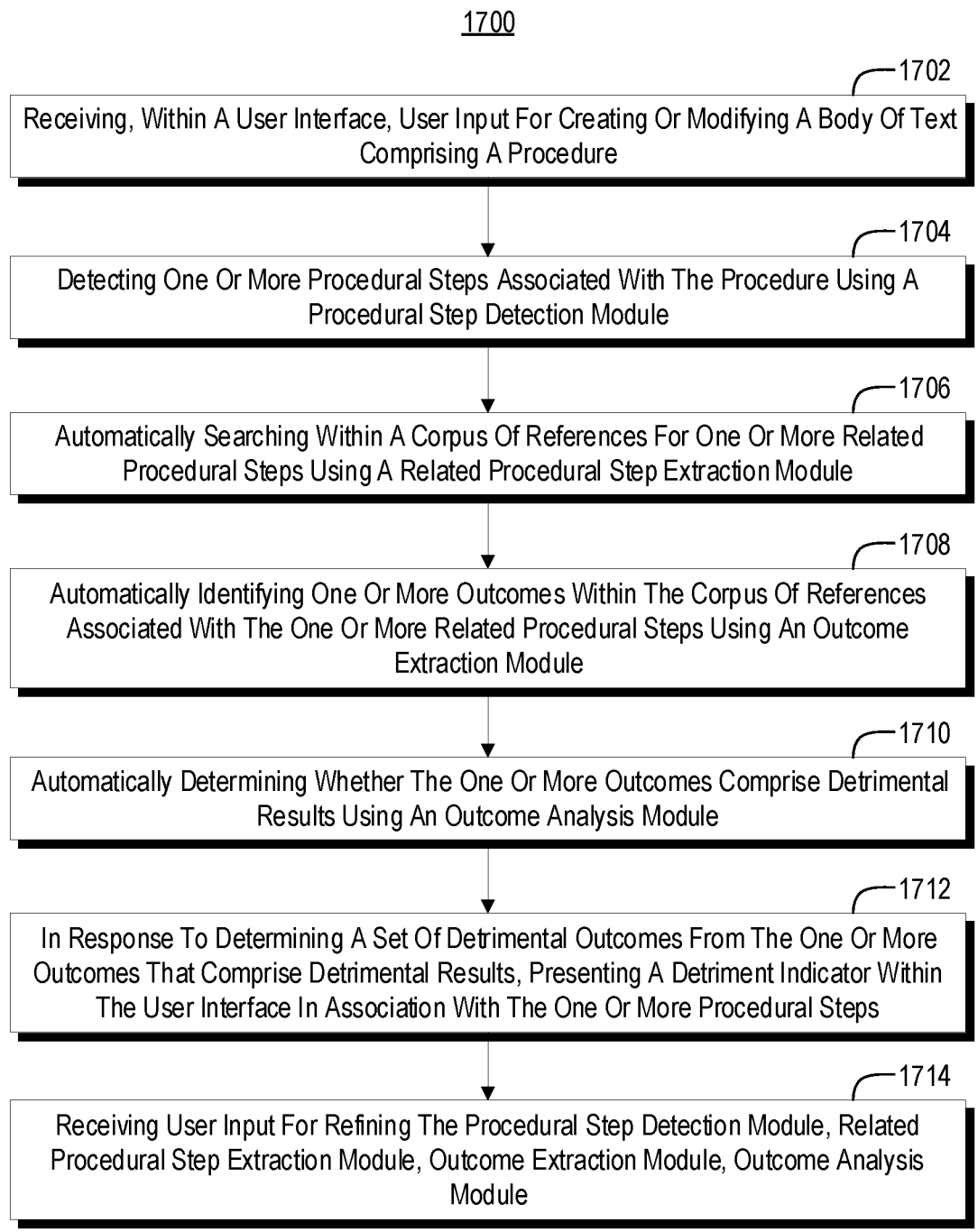
FIGS. 17 and 18 illustrate example flow diagrams depicting acts associated with procedure optimization, in accordance with the present disclosure.
Figure 18:
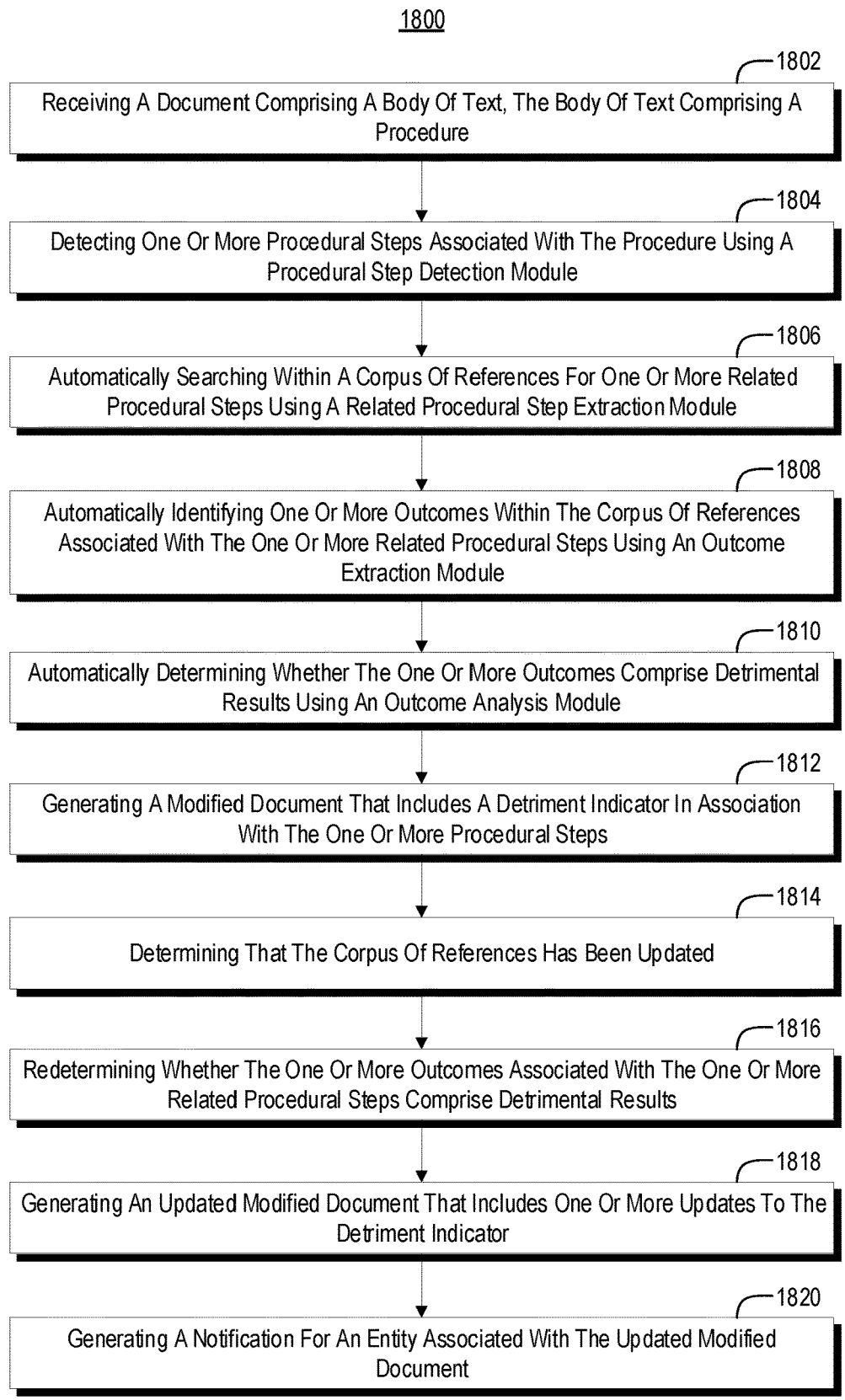

FIGS. 17 and 18 illustrate example flow diagrams 1700 and 1800, respectively, depicting acts associated with procedure optimization, in accordance with the present disclosure.

Act 1702 of flow diagram 1700 includes receiving, within a user interface, user input for creating or modifying a body of text comprising a procedure. Act 1702 is performed, in some instances, by a system 100 utilizing processor(s) 102, storage 104, I/O system(s) 124, communication system(s) 126, and/or other components. The procedure may be associated with any subject matter without limitation, such as clinical trial protocols, standard operating procedures, etc.

Act 1704 of flow diagram 1700 includes detecting one or more procedural steps associated with the procedure using a procedural step detection module. Act 1704 is performed, in some instances, by a system 100 utilizing processor(s) 102, storage 104, procedural step detection module 116, I/O system(s) 124, communication system(s) 126, and/or other components. In some implementations, the procedural step detection module is trained to detect procedural steps within bodies of text.

Act 1706 of flow diagram 1700 includes automatically searching within a corpus of references for one or more related procedural steps using a related procedural step extraction module. Act 1706 is performed, in some instances, by a system 100 utilizing processor(s) 102, storage 104, related procedural step extraction module 118, I/O system(s) 124, communication system(s) 126, and/or other components. In some implementations, the related procedural step extraction module is trained to identify related procedural steps based on content of detected procedural steps. Thus, in some instances, the one or more related procedural steps are determined by the related procedural step extraction module to be relevant to the one or more procedural steps. In some implementations, the one or more related procedural steps identified using the related procedural step extraction module satisfy a threshold of relevance to content of the one or more procedural steps.

Act 1708 of flow diagram 1700 includes automatically identifying one or more outcomes within the corpus of references associated with the one or more related procedural steps using an outcome extraction module. Act 1708 is performed, in some instances, by a system 100 utilizing processor(s) 102, storage 104, outcome extraction module 120, I/O system(s) 124, communication system(s) 126, and/or other components. In some implementations, the outcome extraction module is trained to identify outcomes that are associated with identified procedural steps. In some instances, act 1708 is performed in response to identifying the one or more related procedural steps.

Act 1710 of flow diagram 1700 includes automatically determining whether the one or more outcomes comprise detrimental results using an outcome analysis module. Act 1710 is performed, in some instances, by a system 100 utilizing processor(s) 102, storage 104, outcome analysis module 122, I/O system(s) 124, communication system(s) 126, and/or other components. In some implementations, the outcome analysis module is trained to identify whether results associated with identified outcomes are detrimental.

Act 1712 of flow diagram 1700 includes in response to determining a set of detrimental outcomes from the one or more outcomes that comprise detrimental results, presenting a detriment indicator within the user interface in association with the one or more procedural steps. Act 1712 is performed, in some instances, by a system 100 utilizing processor(s) 102, storage 104, I/O system(s) 124, communication system(s) 126, and/or other components. In some instances, the detriment indicator indicates that the one or more procedural steps are associated with detrimental results. Furthermore, in some instances, the detriment indicator indicates a weight of detriment associated with the one or more procedural steps. In some implementations, the set of detrimental outcomes omits a particular outcome that fails to satisfy a detriment confidence threshold. The detriment confidence threshold indicates a level of confidence in a determination by the outcome analysis module that a result associated with an outcome of a related procedural step is detrimental.

In some implementations act 1712 entails additional acts, such as presenting a representation of the one or more related procedural steps in the user interface in association with the one or more procedural steps, presenting a representation of the set of detrimental outcomes in the user interface in association with the one or more procedural steps, and/or presenting a recommendation for modifying the one or more procedural steps based on the set of detrimental outcomes.

Act 1714 of flow diagram 1700 includes receiving user input for refining the procedural step detection module, related procedural step extraction module, outcome extraction module, outcome analysis module. Act 1714 is performed, in some instances, by a system 100 utilizing processor(s) 102, storage 104, procedural step detection module 116, related procedural step extraction module 118, outcome extraction module 120, outcome analysis module 122, I/O system(s) 124, communication system(s) 126, and/or other components. In some implementations, act 1714 is associated with additional acts, such as receiving user input indicating that a procedural step of the one or more related procedural steps is not relevant to the one or more procedural steps and refining the related procedural step extraction module based on the user input indicating that the procedural step of the one or more related procedural steps is not relevant to the one or more procedural steps.

In some instances, act 1714 includes receiving user input indicating that an outcome of the set of detrimental outcomes is not associated with detrimental results and refining the outcome analysis module based on the user input indicating that the outcome of the set of detrimental outcomes is not associated with detrimental results. Additionally, or alternatively, act 1714 is associated with acts of emphasizing one or more portions of the body of text determined by the procedural step detection module to be contextually associated with the one or more procedural steps, receiving user input modifying the one or more portions of the body of text that are contextually associated with the one or more procedural steps, and refining the procedural step detection module based on the user input modifying the one or more portions of the body of text that are contextually associated with the one or more procedural steps.

Attention is now directed to FIG. 18. Act 1802 of flow diagram 1800 includes receiving a document comprising a body of text, the body of text comprising a procedure. Act 1802 is performed, in some instances, by a system 100 utilizing processor(s) 102, storage 104, I/O system(s) 124, communication system(s) 126, and/or other components.

The document and the body of text may take on various forms as described hereinabove. Furthermore, the procedure may be associated with any subject matter without limitation.

Act 1804 of flow diagram 1800 includes detecting one or more procedural steps associated with the procedure using a procedural step detection module. Act 1804 is performed, in some instances, by a system 100 utilizing processor(s) 102, storage 104, procedural step detection module 116, I/O system(s) 124, communication system(s) 126, and/or other components. In some implementations, the procedural step detection module is trained to detect procedural steps within bodies of text.

Act 1806 of flow diagram 1800 includes automatically searching within a corpus of references for one or more related procedural steps using a related procedural step extraction module. Act 1806 is performed, in some instances, by a system 100 utilizing processor(s) 102, storage 104, related procedural step extraction module 118, I/O system(s) 124, communication system(s) 126, and/or other components. In some implementations, the related procedural step extraction module is trained to identify related procedural steps based on content of detected procedural steps. Thus, in some instances, the one or more related procedural steps are determined by the related procedural step extraction module to be relevant to the one or more procedural steps.

Act 1808 of flow diagram 1800 includes automatically identifying one or more outcomes within the corpus of references associated with the one or more related procedural steps using an outcome extraction module. Act 1808 is performed, in some instances, by a system 100 utilizing processor(s) 102, storage 104, outcome extraction module 120, I/O system(s) 124, communication system(s) 126, and/or other components. In some implementations, the outcome extraction module is trained to identify outcomes that are associated with identified procedural steps. Furthermore, in some instances, act 1808 is performed in response to identifying the one or more related procedural steps.

Act 1810 of flow diagram 1800 includes automatically determining whether the one or more outcomes comprise detrimental results using an outcome analysis module. Act 1810 is performed, in some instances, by a system 100 utilizing processor(s) 102, storage 104, outcome analysis module 122, I/O system(s) 124, communication system(s) 126, and/or other components. In some implementations, the outcome analysis module is trained to identify one or more results associated with identified outcomes and determine whether the one or more results are detrimental.

Act 1812 of flow diagram 1800 includes generating a modified document that includes a detriment indicator in association with the one or more procedural steps. Act 1812 is performed, in some instances, by a system 100 utilizing processor(s) 102, storage 104, I/O system(s) 124, communication system(s) 126, and/or other components. In some implementations, the detriment indicator indicates that the one or more procedural steps are associated with detrimental outcomes. In some instances, act 1812 is performed in response to determining a set of detrimental outcomes from the one or more outcomes that comprise detrimental results.

Act 1814 of flow diagram 1800 includes determining that the corpus of references has been updated. Act 1814 is performed, in some instances, by a system 100 utilizing processor(s) 102, storage 104, I/O system(s) 124, communication system(s) 126, and/or other components. A corpus of references may be updated in various ways as described hereinabove. Furthermore, an update to the corpus of references may be detected in various ways as described hereinabove.

Act 1816 of flow diagram 1800 includes redetermining whether the one or more outcomes associated with the one or more related procedural steps comprise detrimental results. Act 1816 is performed, in some instances, by a system 100 utilizing processor(s) 102, storage 104, related procedural step extraction module 118, outcome extraction module 120, outcome analysis module 122, I/O system(s) 124, communication system(s) 126, and/or other components. In some implementations, act 1816 is performed in response to determining that the corpus of references has been updated.

Act 1818 of flow diagram 1800 includes generating an updated modified document that includes one or more updates to the detriment indicator. Act 1818 is performed, in some instances, by a system 100 utilizing processor(s) 102, storage 104, I/O system(s) 124, communication system(s) 126, and/or other components. The updated modified document may be generated by modifying an existing document or creating a new document.

Act 1820 of flow diagram 1800 includes generate a notification for an entity associated with the updated modified document. Act 1820 is performed, in some instances, by a system 100 utilizing processor(s) 102, storage 104, I/O system(s) 124, communication system(s) 126, and/or other components. The notification may take on various forms and may be delivered in various ways as discussed hereinabove. Furthermore, act 1820 may be performed in response to the updated modified document including the one or more updates to the detriment indicator.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are one or more "physical computer storage media" or "hardware storage device(s)." Computer-readable media that merely carry computer-executable instructions without storing the computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in hardware in the form of computer-executable instructions, data, or data structures and that can be accessed by a general-purpose or special-purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g. as separate threads).

One will also appreciate how any feature or operation disclosed herein may be combined with any one or combination of the other features and operations disclosed herein. Additionally, the content or feature in any one of the figures may be combined or used in connection with any content or feature used in any of the other figures. In this regard, the content disclosed in any one figure is not mutually exclusive and instead may be combinable with the content from any of the other figures.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A system for facilitating optimization of procedures, comprising:
   one or more processors; and
   one or more hardware storage devices storing instructions that are executable by the one or more processors to configure the system to:
   receive, within a user interface, user input for creating or modifying a body of text comprising a procedure;
   detect one or more procedural steps associated with the procedure using a procedural step detection module having been trained to detect procedural steps within bodies of text;
   automatically search within a corpus of references for one or more related procedural steps using a related procedural step extraction module having been trained to identify related procedural steps based on content of detected procedural steps, the one or more related procedural steps being determined by the related procedural step extraction module to be relevant to the one or more procedural steps;
   in response to identifying the one or more related procedural steps, automatically identify one or more outcomes within the corpus of references associated with the one or more related procedural steps using an outcome extraction module having been trained to identify outcomes that are associated with identified procedural steps;
   automatically determine whether the one or more outcomes comprise detrimental results using an outcome analysis module having been trained to identify whether results associated with identified outcomes are detrimental; and
   in response to determining a set of detrimental outcomes from the one or more outcomes that comprise detrimental results, present a detriment indicator within the user interface in association with the one or more procedural steps, the detriment indicator indicating that the one or more procedural steps are associated with detrimental results.

2. The system of claim 1, wherein the detriment indicator indicates a weight of detriment associated with the one or more procedural steps.

3. The system of claim 1, wherein the instructions are executable by the one or more processors to further configure the system to:
present a representation of the one or more related procedural steps in the user interface in association with the one or more procedural steps.

4. The system of claim 3, wherein the instructions are executable by the one or more processors to further configure the system to:
receive user input indicating that a procedural step of the one or more related procedural steps is not relevant to the one or more procedural steps; and
refine the related procedural step extraction module based on the user input indicating that the procedural step of the one or more related procedural steps is not relevant to the one or more procedural steps.

5. The system of claim 1, wherein the instructions are executable by the one or more processors to further configure the system to:
present a representation of the set of detrimental outcomes in the user interface in association with the one or more procedural steps.

6. The system of claim 5, wherein the instructions are executable by the one or more processors to further configure the system to:
receive user input indicating that an outcome of the set of detrimental outcomes is not associated with detrimental results; and
refine the outcome analysis module based on the user input indicating that the outcome of the set of detrimental outcomes is not associated with detrimental results.

7. The system of claim 1, wherein the set of detrimental outcomes omits a particular outcome that fails to satisfy a detriment confidence threshold, the detriment confidence threshold indicating a level of confidence in a determination by the outcome analysis module that a result associated with an outcome of a related procedural step is detrimental.

8. The system of claim 1, wherein the instructions are executable by the one or more processors to further configure the system to:
present a recommendation for modifying the one or more procedural steps based on the set of detrimental outcomes.

9. The system of claim 1, wherein the instructions are executable by the one or more processors to further configure the system to:
emphasize one or more portions of the body of text determined by the procedural step detection module to be contextually associated with the one or more procedural steps;
receive user input modifying the one or more portions of the body of text that are contextually associated with the one or more procedural steps; and
refine the procedural step detection module based on the user input modifying the one or more portions of the body of text that are contextually associated with the one or more procedural steps.

10. The system of claim 1, wherein the one or more related procedural steps identified using the related procedural step extraction module satisfy a threshold of relevance to content of the one or more procedural steps.

11. The system of claim 1, the procedure being associated with a clinical trial protocol.

12. A system for facilitating optimization of procedures, comprising:
one or more processors; and
one or more hardware storage devices storing instructions that are executable by the one or more processors to configure the system to:
receive a document comprising a body of text, the body of text comprising a procedure;
detect one or more procedural steps associated with the procedure using a procedural step detection module having been trained to detect procedural steps within bodies of text;
automatically search within a corpus of references for one or more related procedural steps using a related procedural step extraction module having been trained to identify related procedural steps based on content of detected procedural steps, the one or more related procedural steps being determined by the related procedural step extraction module to be relevant to the one or more procedural steps;
in response to identifying the one or more related procedural steps, automatically identify one or more outcomes within the corpus of references associated with the one or more related procedural steps using an outcome extraction module having been trained to identify outcomes that are associated with identified procedural steps;
automatically determine whether the one or more outcomes comprise detrimental results using an outcome analysis module having been trained to identify one or more results associated with identified outcomes and determine whether the one or more results are detrimental; and
in response to determining a set of detrimental outcomes from the one or more outcomes that comprise detrimental results, generate a modified document that includes a detriment indicator in association with the one or more procedural steps, the detriment indicator indicating that the one or more procedural steps are associated with detrimental outcomes.

13. The system of claim 12, wherein the instructions are executable by the one or more processors to further configure the system to:
determine that the corpus of references has been updated;
in response to determining that the corpus of references has been updated, redetermining whether the one or more outcomes associated with the one or more related procedural steps comprise detrimental results; and
generate an updated modified document that includes one or more updates to the detriment indicator.

14. The system of claim 13, wherein the instructions are executable by the one or more processors to further configure the system to:
in response to the updated modified document including the one or more updates to the detriment indicator, generate a notification for an entity associated with the updated modified document.

15. A method for facilitating optimization of procedures, comprising:
receiving, within a user interface, user input for creating or modifying a body of text comprising a procedure;
detecting one or more procedural steps associated with the procedure using a procedural step detection module having been trained to detect procedural steps within bodies of text;
automatically searching within a corpus of references for one or more related procedural steps using a related procedural step extraction module having been trained to identify related procedural steps based on content of detected procedural steps, the one or more related procedural steps being determined by the related procedural step extraction module to be relevant to the one or more procedural steps;

in response to identifying the one or more related procedural steps, automatically identifying one or more outcomes within the corpus of references associated with the one or more related procedural steps using an outcome extraction module having been trained to identify outcomes that are associated with identified procedural steps;

automatically determining whether the one or more outcomes comprise detrimental results using an outcome analysis module having been trained to identify one or more results associated with identified outcomes and determine whether the one or more results are detrimental; and in response to determining a set of detrimental outcomes from the one or more outcomes that comprise detrimental results, presenting a detriment indicator within the user interface in association with the one or more procedural steps, the detriment indicator indicating that the one or more procedural steps are associated with detrimental results.

16. The method of claim 15, wherein the detriment indicator indicates a weight of detriment associated with the one or more procedural steps.

17. The method of claim 15, further comprising:
presenting a representation of the one or more related procedural steps in the user interface in association with the one or more procedural steps.

18. The method of claim 17, further comprising:
receiving user input indicating that a procedural step of the one or more related procedural steps is not relevant to the one or more procedural steps; and
refining the related procedural step extraction module based on the user input indicating that the procedural step of the one or more related procedural steps is not relevant to the one or more procedural steps.

19. The method of claim 15, further comprising:
presenting a representation of the set of detrimental outcomes in the user interface in association with the one or more procedural steps.

20. The method of claim 19, further comprising:
receiving user input indicating that an outcome of the set of detrimental outcomes is not associated with detrimental results; and
refining the outcome analysis module based on the user input indicating that the outcome of the set of detrimental outcomes is not associated with detrimental results.

* * * * *